US007132536B2

(12) United States Patent
Weichert et al.

(10) Patent No.: US 7,132,536 B2
(45) Date of Patent: Nov. 7, 2006

(54) TRIAZA- AND TETRAAZA-ANTHRACENEDIONE DERIVATIVES, THEIR PREPARATION AND THEIR USE AS PHARMACEUTICALS

(75) Inventors: Andreas Weichert, Norderstedt (DE); Hartmut Strobel, Liederbach (DE); Paulus Wohlfart, Bensheim (DE); Marcel Patek, Tucson, AZ (US); Martin Smrcina, Tucson, AZ (US); Aleksandra Weichsel, Tucson, AZ (US)

(73) Assignee: Sanofi-aventis Deutschland GmbH, Frankfurt (DE)

( * ) Notice: Subject to any disclaimer, the term of this patent is extended or adjusted under 35 U.S.C. 154(b) by 0 days.

(21) Appl. No.: 10/829,064

(22) Filed: Apr. 21, 2004

(65) Prior Publication Data

US 2004/0248900 A1 Dec. 9, 2004

Related U.S. Application Data

(60) Provisional application No. 60/499,521, filed on Sep. 2, 2003.

(30) Foreign Application Priority Data

Apr. 24, 2003 (EP) ................... 03009286

(51) Int. Cl.
C07D 471/14 (2006.01)
(52) U.S. Cl. .............. 544/250; 544/251; 514/250
(58) Field of Classification Search ............. 514/250; 544/250, 251, 252
See application file for complete search history.

(56) References Cited

U.S. PATENT DOCUMENTS

| 3,905,976 | A | * | 9/1975 | Hardtmann ............. 544/250 |
| 4,162,319 | A | * | 7/1979 | Seubert et al. .......... 514/250 |
| 5,605,905 | A | * | 2/1997 | Avendano et al. ........ 514/292 |
| 6,617,359 | B1 | | 9/2003 | Wohlfart et al. ......... 514/617 |
| 6,759,412 | B1 | * | 7/2004 | Strobel et al. ........ 514/235.5 |
| 2002/0143007 | A1 | * | 10/2002 | Garvey et al. .......... 514/218 |
| 2003/0022935 | A1 | * | 1/2003 | Strobel et al. .......... 514/522 |
| 2003/0055093 | A1 | * | 3/2003 | Strobel et al. .......... 514/367 |

FOREIGN PATENT DOCUMENTS

WO WO 99/47153 9/1999
WO WO 00/03746 1/2000

OTHER PUBLICATIONS

Driver, et al., A Second-Generation Catalyst for Aryl Halide Amination: Mixed Secondary Amines from Aryl Halides and Primary Amines Catalyzed by (DPPF)PdCl2, J. AMer. Chem Soc.; 118; 1996; pp. 7217-7218.

Endres, et al., Stroke Protection By 3-Hydroxy-3-Methylglutaryl (HMG)—CoA Reductase Inhibitors Medicated By Endothelial Nitric Oxide Synthase, Proc. Natl. Acad. Sci. USA, 95 (1998) 8880-8885.

Ll Huige et al., Activation of Protein Kinase C(alpha) and/or (epsilon) Enhances Transcription of the Human Endothelial Nitric Oxide Synthase Gene, Mol. Pharmacol., 1998,vol. 53, pp. 630-637.

Martin-Santamaria, et al., Synthesis and Stereochemistry of 11,11a-Dihydro Derivatives of (4S)-2,4-Dimethyl-2,4dihydro-1H-pyrazino[2,1-b]quinazoline-3,6-diones. A New Transannular Rearrangement Proposal., J. Org.Chem.; 64; 1999; pp. 7233-7235.

Moroi, et al. , Interaction of Genetic Deficiency of Endothelial Nitric Oxide, Gender, and Pregnancy in Vascular Response to Injury in Mice, J. Clin. Invest., 101 (1998) 1225-1232.

Nakayama Masafumi et al., T-786→C Mutation in the 5'-Flanking Region of the Endothelial Ntric Oxide Synthase Gene Is Associated with Coronary Spasm, Clinical Investigation and Reports, Circulation 99, 1999, pp. 2864-2870.

Sessa, et al., Chronic Exercise In Dogs Increases Coronary Vascular Nitric Oxide Production And Endothelial Cell Nitric Oxide Synthase Gene Expression, Circ. Research 74 (1994) 349-353.

Varenne, et al. , Percutaneous Gene Therapy Using Recombinant Adenoviruses Encoding Human Herpes Simplex Virus Thymidine Kinase, Human PAI-1, and Human NOS3 In Balloon-Injured Porcine Coronary Arteries, Hum. Gene Ther. 11 (2000) 1329-1339.

(Continued)

Primary Examiner—Thomas C. McKenzie
(74) Attorney, Agent, or Firm—Jiang Lin

(57) ABSTRACT

The present invention relates to triaza- and tetraaza-anthracenedione derivatives of the formula I,

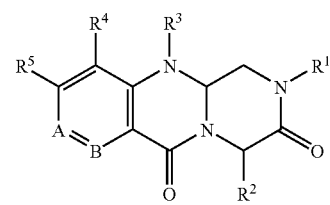

wherein A, B and $R^1$ to $R^5$ are as defined herein. The compounds of formula I are valuable pharmacologically active compounds. They are useful in the treatment of various disease states including cardiovascular disorders such as atherosclerosis, thrombosis, coronary artery disease, hypertension and cardiac insufficiency. They upregulate the expression of the enzyme endothelial nitric oxide (NO) synthase and can be applied in conditions in which an increased expression of said enzyme or an increased NO level or the normalization of a decreased NO level is desired. The invention furthermore relates to processes for the preparation of compounds of the formula I, their use, in particular as active ingredients in pharmaceuticals, and pharmaceutical preparations comprising them.

8 Claims, No Drawings

OTHER PUBLICATIONS

Vojkovsky, et al., Solid-Phase Synthesis of Heterocycles Containing an 1-Acyl-3-oxopiperazine Skeleton, J. Org. Chem.; 63; 1998; pp. 3162-3163.
U.S. Appl. No. 10/146,671, filed May 16, 2002, Garvey et al.
U.S. Appl. No. 10/073,160, filed Feb. 13, 2002, Strobel.
U.S. Appl. No. 10/073,203, filed Feb. 13, 2002, Strobel.
U.S. Appl. No. 10/073,307, filed Feb. 13, 2002, Strobel.

* cited by examiner

TRIAZA- AND TETRAAZA-ANTHRACENEDIONE DERIVATIVES, THEIR PREPARATION AND THEIR USE AS PHARMACEUTICALS

This application claims the benefit of U.S. Provisional Application No. 60/499,521, filed Sep. 2, 2003.

FIELD OF THE INVENTION

The present invention relates to triaza- and tetraaza-anthracenedione derivatives of the formula I,

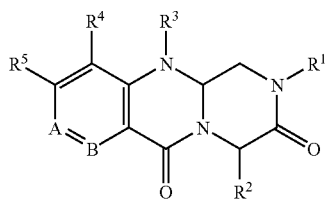

in which A, B and $R^1$ to $R^5$ have the meanings indicated below. The compounds of formula I are valuable pharmacologically active compounds. They are useful in the treatment of various disease states including cardiovascular disorders such as atherosclerosis, thrombosis, coronary artery disease, hypertension and cardiac insufficiency. They upregulate the expression of the enzyme endothelial nitric oxide (NO) synthase and can be applied in conditions in which an increased expression of said enzyme or an increased NO level or the normalization of a decreased NO level is desired. The invention furthermore relates to processes for the preparation of compounds of the formula I, their use, in particular as active ingredients in pharmaceuticals, and pharmaceutical preparations comprising them.

BACKGROUND OF THE INVENTION

Endothelial NO synthase (eNOS, NOS-III) belongs to a group of three isoenzymes that produce nitric oxide (nitrogen monoxide, NO) by oxidation of arginine. Endothelially released NO is of central importance in a number of key cardiovascular mechanisms. It has a vasodilating effect and inhibits the aggregation of platelets, the adhesion of leukocytes to the endothelium and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349) were able to obtain a marked increase in eNOS by means of exercise training and the increase in shear stress associated therewith.

Whether regulation at the post-transcriptional level is relevant in vivo, has not been unambiguously proven. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides to the lipid lowering, also in part to an increase in eNOS expression in vivo (Endres et al., Proc. Natl. Acad. Sci. USA 95 (1998) 8880). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension that may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329).

Some low molecular weight compounds that, in cell cultures, may lead to a direct effect on eNOS transcription and expression are disclosed in the literature. For the statins, as has already been mentioned, it has been possible to show such an increase in eNOS in vivo as a side effect. In view of the known range of side effects of this class of substances, however, it is unclear how far use of this effect can be made in a toxicologically unproblematic dose. Liao et al. claim in WO 99/47153 and WO 00/03746 the use of rhoGTPase inhibitors and agents which influence the organization of the actin cytoskeleton for increasing eNOS in endothelial cells and for the therapy of various disorders such as, for example, strokes or pulmonary hypertension without, however, indicating a specific way of achieving this. Certain compounds of the N-benzocycloalkenyl amide type which upregulate the expression of endothelial NO synthase have been described in WO 02/064146, WO 02/064545, WO 02/064546 and WO 02/064565.

There still exists a strong need for further compounds which upregulate eNOS expression in endothelial cells. Surprisingly it has now been found that the triaza- and tetraaza-anthracenedione derivatives of formula I upregulate eNOS expression and are useful in the treatment of various disease states such as cardiovascular disorders.

Compounds of the formula I that are similar to the compounds according to the present invention, specifically the compound of the formula I in which simultaneously A is C—NO$_2$, B is CH, R$^1$ is benzyl, R$^2$ is methyl, R$^3$ is isopropyl and R$^4$ and R$^5$ are hydrogen, and the compound of formula I in which simultaneously A is C—NO$_2$, B is CH, R$^1$ is 2-methoxyethyl, R$^2$ is benzyl, R$^3$ is isopropyl and R$^4$ and R$^5$ are hydrogen, have already been obtained by Vojkovsky et al. (J. Org. Chem. 63 (1998) 3162) during investigations on N-acyliminium ion reactions. However, any biological activities of these two compounds have not been described. This also applies for the compound of the formula I in which simultaneously A and B are CH, R$^1$ and R$^2$ are methyl, R$^3$ is benzyl, i.e. unsubstituted —CH$_2$-phenyl, and R$^4$ and R$^5$ are hydrogen, which has been prepared by Martin-Santamaria et al. (J. Org. Chem. 64 (1999) 7233 during investigations on rearrangement reactions.

SUMMARY OF THE INVENTION

A subject of the present invention are compounds of the formula I,

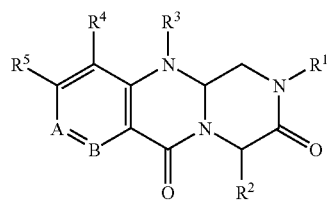

in which

A is CR$^6$ or N and B is CR$^7$ or N, but A and B are not simultaneously N;

R$^1$ is (C$_1$–C$_{10}$)-alkyl, (C$_3$–C$_8$)-cycloalkyl, (C$_2$–C$_{10}$)-alkenyl or (C$_2$–C$_{10}$)-alkynyl which are all unsubstituted or substituted by one or more identical or different substituents selected from the group consisting of halogen, cyano, (C$_3$–C$_8$)-cycloalkyl, phenyl, biphenylyl, naphthyl, indanyl and heteroaryl;

R$^2$ is hydrogen, (C$_1$–C$_4$)-alkyl, trifluoromethyl, —(CH$_2$)$_a$-(C$_3$–C$_8$)-cycloalkyl, —(CH$_2$)$_a$-phenyl, —(CH$_2$)$_a$-imidazolyl or —(CH$_2$)$_a$-pyridinyl, wherein a is 0, 1 or 2;

R$^3$ is —(CH$_2$)$_b$-phenyl, —(CH$_2$)$_b$-imidazolyl, —(CH$_2$)$_b$-triazolyl, —(CH$_2$)$_b$-Het or —(CH$_2$)$_b$-pyridinyl, wherein b is 1, 2, 3 or 4;

R$^4$, R$^5$, R$^6$ and R$^7$ which are independent of one another and can be identical or different, are selected from the group consisting of hydrogen, (C$_1$–C$_4$)-alkyl, trifluoromethyl, (C$_1$–C$_4$)-alkoxy, trifluoromethoxy, halogen, nitro, cyano, —CO—R$^{10}$, —NR$^8$R$^9$, —NH—CO—(C$_1$–C$_4$)-alkyl, —SO$_2$—NR$^8$R$^9$, —SO$_2$—(C$_1$–C$_4$)-alkyl and —SO$_2$—(CH$_2$)$_c$-phenyl, wherein c is 0, 1 or 2;

R$^8$ and R$^9$ which are independent of one another and can be identical or different, are selected from the group consisting of hydrogen and (C$_1$–C$_4$)-alkyl;

R$^{10}$ is hydroxy, (C$_1$–C$_4$)-alkoxy or —NR$^8$R$^9$,

Het is a residue of a saturated 4-membered to 8-membered monocyclic heterocycle which contains a ring nitrogen atom via which it is bonded, and which additionally can contain a further ring heteroatom selected from the group consisting of N, O and S, and which is unsubstituted or substituted by one or more identical or different substituents selected from the group consisting of (C$_1$–C$_4$)-alkyl and —(CH$_2$)$_d$-phenyl, wherein d is 0, 1 or 2;

heteroaryl is a residue of an aromatic 5-membered to 10-membered, monocyclic or bicyclic heterocycle which contains 1, 2, 3 or 4 identical or different ring heteroatoms selected from the group consisting of N, O and S;

where all residues phenyl, biphenylyl, naphthyl, indanyl, heteroaryl, pyridinyl, imidazolyl and triazolyl in each case are unsubstituted or are independently of one another substituted by one or more identical or different substituents selected from the group consisting of halogen, cyano, (C$_1$–C$_6$)-alkyl, trifluoromethyl, (C$_1$–C$_6$)-alkoxy and trifluoromethoxy;

in all their stereroisomeric forms and mixtures thereof in any ratio, and their physiologically acceptable salts;

provided that R$^3$ cannot be unsubstituted —CH$_2$-phenyl when simultaneously A and B are CH, R$^1$ and R$^2$ are methyl, and R$^4$ and R$^5$ are hydrogen.

DETAILED DESCRIPTION OF THE INVENTION

Definition of Terms

As used above, and throughout the description of the invention, the following terms, unless otherwise indicated, shall be understood to have the following meanings.

If in the compounds of formula I groups, substituents or heteroatoms such as, for example, R$^8$, R$^9$, alkyl, phenyl, heteroaryl, etc., can be present several times, they can all independently of one another have the meanings indicated and can hence in each case be identical or different from one another. As an example a dialkylamino group may be mentioned in which the alkyl substitutents can be identical or different.

If a number a, c or d is zero, the two groups which are attached to the group (CH$_2$)$_a$, (CH$_2$)$_c$ or (CH$_2$)$_d$, respectively, are connected to one another via a direct bond.

Alkyl, alkenyl and alkynyl groups can be linear (i.e. straight-chain) or branched. This also applies when they are part of other groups, for example alkoxy groups, i.e. alkyl-O— groups, alkoxycarbonyl groups or alkyl-substituted amino groups, or when they are substituted. Substituted alkyl, alkenyl and alkynyl groups can be substituted by one or more, for example one, two, three, four or five, identical or different substituents which can be located in any desired positions. Examples of alkyl groups are methyl, ethyl, propyl, butyl, pentyl, hexyl, heptyl, octyl, nonyl, decyl, the n-isomers of these residues, isopropyl, isobutyl, isopentyl, sec-butyl, tert-butyl, neopentyl or 3,3-dimethylbutyl. Alkenyl groups and alkynyl groups preferably contain one double bond or triple bond, respectively, which can be present in any desired position of the group. Examples of alkenyl and alkynyl are ethenyl (=vinyl), prop-1-enyl, prop-2-enyl (=allyl), but-2-enyl, 2-methylprop-2-enyl, 3-methylbut-2-enyl, hex-3-enyl, hex-4-enyl, 4-methylhex-4-enyl, dec-3-enyl, dec-9-enyl, ethynyl, prop-2-ynyl (=propargyl), but-2-ynyl, but-3-ynyl, hex-4-ynyl or hex-5-ynyl.

Examples of cycloalkyl groups are cyclopropyl, cyclobutyl, cyclopentyl, cyclohexyl, cycloheptyl or cyclooctyl which, in general, can all also carry one or more, for example one, two, three or four, identical or different $(C_1–C_4)$-alkyl substituents, for example methyl substituents, which can be located in any desired positions. Examples of substituted cycloalkyl groups are 4-methylcyclohexyl, 4-tert-butylcyclohexyl or 2,3-dimethylcyclopentyl.

Naphthyl, biphenylyl, indanyl, heteroaryl, pyridinyl, imidazolyl and triazolyl groups can be bonded via any desired position. Naphthyl can be naphth-1-yl or naphth-2-yl. Biphenylyl can be biphenyl-2-yl, biphenyl-3-yl or biphenyl-4-yl. Indanyl can be bonded via any carbon atom in the 6-membered ring or in the 5-membered ring and can be indan-1-yl, indan-2-yl, indan-3-yl, indan-4-yl, indan-5-yl, indan-6-yl or indan-7-yl. Pyridinyl can be pyridin-2-yl, pyridin-3-yl or pyridin-4-yl. Heteroaryl, imidazolyl and triazolyl groups can be bonded via a ring carbon atom or a ring nitrogen atom. Imidazolyl can be, for example, 1H-imidazol-1-yl, 1H-imidazol-2-yl, 1H-imidazol-4-yl or 1H-imidazol-5-yl. Triazolyl can be 1,2,3-triazolyl and more specifically, for example, 1H-1,2,3-triazol-1-yl, 1H-1,2,3-triazol-4-yl or 1H-1,2,3-triazol-5-yl, or it can be 1,2,4-triazolyl and more specifically, for example, 1H-1,2,4-triazol-1-yl or 1H-1,2,4-triazol-3-yl.

Substituted phenyl, naphthyl, biphenylyl, indanyl, heteroaryl, pyridinyl, imidazolyl and triazolyl groups can be substituted on ring carbon atoms and/or on ring nitrogen atoms by one or more, for example one, two, three or four, identical or different substituents which can be located in any desired positions. In monosubstituted phenyl groups the substituent can be located in the 2-position, the 3-position or the 4-position. In a disubstituted phenyl group the substituents can be located in 2,3position, 2,4-position, 2,5-position, 2,6-position, 3,4-position or 3,5-position. In trisubstituted phenyl groups the substituents can be located in 2,3,4-position, 2,3,5-position, 2,3,6-position, 2,4,5-position, 2,4, 6-position, or 3,4,5-position. In monosubstituted naphth-1-yl groups the substituent can be located in the 2-, 3-, 4-, 5-, 6-, 7-, or 8-position, in monosubstituted naphth-2-yl groups the substituent can be located in the 1-, 3-, 4-, 5-, 6-, 7-, or 8-position. In monosubstituted pyridin-2-yl the substituent can be located in the 3-position, 4-position, 5-position or 6-position, in monosubstituted pyridin-3-yl the substituent can be located in the 2-position, 4-position, 5-position or 6-position, in monosubstituted pyridin-4-yl the substituent can be located in the 2-position or 3-position.

Heteroaryl groups are preferably derived from 5-membered or 6-membered monocyclic aromatic heterocycles or 9-membered or 10-membered bicyclic aromatic heterocycles where the bicyclic heterocycles contain a 6-membered ring condensed to a 5-membered or two condensed 6-membered rings and where in the bicyclic heterocycles one or both rings can be aromatic and one or both rings can contain ring heteroatoms. Preferably heteroaryl groups contain 1, 2 or 3, for example 1 or 2, identical or different ring heteroatoms. The ring heteroatoms in any heterocycles can be located in any desired positions provided that the resulting heterocyclic system is known in the art and is stable and suitable as a subgroup in a drug substance. Examples of aromatic heterocycles from which a heteroaryl group can be derived, are pyrrole, furan, thiophene, imidazole, pyrazole, 1,2,3-triazole, 1,2,4-triazole, 1,3-oxazole (=Oxazole), 1,2-oxazole (=isoxazole), 1,3-thiazole (=thiazole), 1,2-thiazole (=isothiazole), tetrazole, pyridine, pyridazine, pyrimidine, pyrazine, 1,2,3-triazine, 1,2,4-triazine, 1,3,5-triazine, 1,2,4, 5-tetrazine, indole, benzothiophene, benzofuran, 1,3-benzo-dioxole (=1,2-methylenedioxybenzene), 1,3-benzoxazole, 1,3-benzothiazole, benzimidazole, chroman, isochroman, 1,4-benzodioxane (=1,2-ethylenedioxybenzene), quinoline, isoquinoline, cinnoline, quinazoline, quinoxaline, phthalazine, thienothiophenes, 1,8-naphthyridine and other naphthyridines, or pteridine. As already mentioned and as specified with respect to pyridinyl, imidazolyl and triazolyl groups, heteroaryl groups can be bonded via any desired ring carbon atom and, in the case of nitrogen heterocycles, via any desired suitable ring nitrogen atom. For example, furanyl can be furan-2-yl or furan-3-yl, thiophenyl (=thienyl) can be thiophen-2-yl or thiophen-3-yl, pyrazolyl can be pyrazol-1-yl, pyrazol-3-yl, pyrazol-4-yl or pyrazol-5-yl, quinolinyl can be quinolin-2-yl, quinolin-3-yl, quinolin-4-yl, quinolin-5-yl, quinolin-6-yl, quinolin-7-yl or quinolin-8-yl. As likewise already mentioned, and as specified with respect to pyridinyl groups, substituted heteroaryl groups can be substituted on any desired ring carbon atoms and/or on ring nitrogen atoms by one or more identical or different substituents where preferred substituents on ring nitrogen atoms of substituted heteroaryl groups are alkyl groups, for example $(C_1–C_4)$-alkyl groups. Suitable ring nitrogen atoms in heteroaryl groups, including pyridinyl, imidazolyl and triazolyl groups, as well as nitrogen atoms representing the groups A and B in formula I can also be present as N-oxides or as quaternary salts, the latter preferably having a counter-anion which is derived from a physiologically acceptable acid.

Het groups which are bonded via a ring nitrogen atom and which thus contain at least one ring nitrogen atom, are derived from 4-membered, 5-membered, 6-membered, 7-membered or 8-membered saturated monocyclic heterocycles, preferably from 5-membered, 6-membered or 7-membered heterocycles, particularly preferably from 5-membered or 6-membered heterocycles. Examples of Het which contain one ring heteroatom are azetidin-1-yl, pyrrolidin-1-yl, piperidin-1-yl, perhydroazepin-1-yl and perhydroazocin-1-yl. Examples of Het which contain two ring heteroatoms are pyrazolidin-1-yl, imidazolidin-1-yl, 1,2-oxazolidin-2-yl, 1,3-oxazolidin-3-yl, 1,3-thiazolidin-3-yl, piperazin-1-yl, perhydro-1,2-oxazin-2-yl, perhydro-1,3-oxazin-3-yl, morpholin-4-yl, thiomorpholin-4-yl, perhydro-1,3-diazepin-1-yl, perhydro-1,4-diazepin-1-yl, perhydro-1,4-oxazepin-4-yl, or perhydro-1,4-thiazepin-4-yl. Substituted Het groups can be substituted on ring carbon atoms and/or on a second ring nitrogen atom, when present, by one or more, for example one, two, three, four or five, identical or different substituents which can be located in any desired positions. Examples of substituted Het groups are 2,2-dimethylpiperidin-1-yl, 2,6-dimethylpiperidin-1-yl, 4-benzyl-2,2-dimethylpiperazin-1-yl or 4-(3-methoxyphenyl)piperazin-1-yl. Ring nitrogen atoms in Het groups can also be present as quaternary salts which preferably have a counter-anion which is derived from a physiologically acceptable acid. Ring sulfur atoms can also be oxidized to the sulfoxide or to the sulfone. Thus, for example, a thiomorpholinyl group may be present as 1-oxo-thiomorpholin-4-yl or 1,1-dioxo-thiomorpholin-4-yl.

Halogen is fluorine, chlorine, bromine or iodine, preferably fluorine, chlorine or bromine.

Patient includes both human and other mammals.

Pharmaceutically effective amount means an amount of the compound according to the invention effective in producing the desired therapeutic effect.

The present invention includes all stereoisomeric forms of the compounds of the formula I and their salts. With respect to each chiral center, independently from any other chiral center, the compounds of formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention that can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings, the invention includes both the E form and Z form, or the cis form and the trans form, as well as mixtures of these forms in all ratios. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally a derivatization can be carried out before a separation of stereoisomers. The separation of a mixture of stereoisomers can be carried out at the stage of the compounds of the formula I or at the stage of a starting material or an intermediate during the synthesis. The present invention also includes all tautomeric forms of the compounds of formula I and their salts.

In case the compounds of the formula I contain one or more acidic and/or basic groups, the invention also comprises their corresponding physiologically or toxicologically acceptable salts, in particular their pharmaceutically acceptable salts. Thus, the compounds of the formula I that contain an acidic group can be present on such groups and can be used according to the invention, for example, as alkali metal salts, alkaline earth metal salts or as ammonium salts. More specific examples of such salts include sodium salts, potassium salts, calcium salts, magnesium salts, quaternary ammonium salts such as tetraalkylammonium salts, or acid addition salts with ammonia or organic amines such as, for example, ethylamine, ethanolamine, triethanolamine or amino acids. Compounds of the formula I that contain a basic group, i.e. a group which can be protonated, can be present on such groups and can be used according to the invention, for example, in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, nicotinic acid, isonicotinic acid, citric acid, adipic acid, and other acids known to the person skilled in the art. If the compounds of the formula I simultaneously contain acidic and basic groups in the molecule, the invention also includes, in addition to the salt forms mentioned, inner salts or betaines or zwitterions. The salts of the compounds of the formula I can be obtained by customary methods which are known to the person skilled in the art like, for example by contacting the compound of the formula I with an organic or inorganic acid or base in a solvent or diluent, or by anion exchange or cation exchange from another salt. The present invention also includes all salts of the compounds of the formula I which, owing to low physiological compatibility, are not directly suitable for use in pharmaceuticals but which can be used, for example, as intermediates for chemical reactions or for the preparation of physiologically acceptable salts.

The present invention furthermore includes all solvates of compounds of the formula I, for example hydrates or adducts with alcohols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

Particular or Preferred Embodiments

In one embodiment of the invention the group A is $CR^6$ and the group B is $CR^7$. In another embodiment of the invention one of the groups A and B is nitrogen, i.e. the group A is $CR^6$ and the group B is N or the group A is N and the group B is $CR^7$.

$R^1$ preferably is $(C_1-C_6)$-alkyl which is unsubstituted or substituted by one or more identical or different substituents selected from the group consisting of $(C_3-C_6)$—cycloalkyl, phenyl, biphenylyl, naphthyl, indanyl, thienyl and pyridinyl, where phenyl, biphenylyl, naphthyl, indanyl, thienyl and pyridinyl are unsubstituted or substituted as indicated above. More preferably $R^1$ is $(C_1-C_6)$-alkyl that is substituted by one or more, in particular by one, substituent selected from the group consisting of phenyl and naphthyl, where phenyl and naphthyl are unsubstituted or substituted as indicated above. Particularly preferably $R^1$ is $(C_1-C_6)$-alkyl that is substituted by a phenyl group, where the phenyl group is unsubstituted or substituted as indicated above. More particularly preferably $R^1$ is benzyl or phenyl-substituted butyl, in particular benzyl or 4-phenylbutyl-, where in the benzyl and phenylbutyl- groups the phenyl group is unsubstituted or substituted as indicated above.

Substituted phenyl, biphenylyl, naphthyl, indanyl, thienyl and pyridinyl groups present in the group $R^1$ are preferably substituted by one or more, for example one or two, identical or different substituents selected from the group consisting of fluorine, chlorine, bromine, cyano, $(C_1-C_4)$-alkyl, trifluoromethyl, $(C_1-C_4)$-alkoxy and trifluoromethoxy, more preferably from the group consisting of $(C_1-C_4)$-alkyl, trifluoromethyl, $(C_1-C_4)$-alkoxy and trifluoromethoxy.

In one embodiment of the invention $R^2$ preferably is hydrogen, $(C_1-C_4)$-alkyl, trifluoromethyl, $—(CH_2)_a$-$(C_3-C_6)$-cycloalkyl, $—(CH_2)_a$-phenyl, $—CH_2$-imidazolyl or $—CH_2$-pyridinyl, wherein a is 0, 1 or 2, preferably 0 or 1, and where phenyl, imidazolyl and pyridinyl are unsubstituted or substituted as indicated above. More preferably $R^2$ is hydrogen, $(C_1-C_4)$-alkyl, trifluoromethyl, $(C_3-C_6)$-cycloalkyl, $—(CH_2)_a$-phenyl, $—CH_2$-imidazolyl or $—CH_2$-pyridinyl, wherein a is 0 or 1 and where phenyl, imidazolyl and pyridinyl are unsubstituted or substituted as indicated above. Particularly preferably $R^2$ is hydrogen, $(C_1-C_4)$-alkyl, trifluoromethyl, $(C_3-C_6)$-cycloalkyl or $—CH_2$-phenyl, where the phenyl group is unsubstituted or substituted as indicated above. More particularly preferably $R^2$ is hydrogen, $(C_1-C_4)$-alkyl, trifluoromethyl or $(C_3-C_6)$-cycloalkyl. In another embodiment of the invention $R^2$ has the mentioned general or preferred meanings with the exception of hydrogen. Especially preferably $R^2$ is $(C_1-C_4)$-alkyl, for example ethyl or isopropyl, or $(C_3-C_6)$-cycloalkyl, for example cyclopropyl or cyclohexyl, more especially preferably $(C_1-C_4)$-alkyl.

An imidazolyl group present in $R^2$ preferably is imidazol-4-yl, a pyridinyl group present in $R^2$ preferably is pyridin-3-yl. Substituted phenyl, imidazolyl and pyridinyl groups present in the group $R^2$ are preferably substituted by one or more, for examples one or two, identical or different substituents selected from the group consisting of fluorine, chlorine, bromine, $(C_1-C_4)$-alkyl, trifluoromethyl, $(C_1-C_4)$-alkoxy and trifluoromethoxy, more preferably from fluorine, chlorine, bromine, $(C_1-C_4)$-alkyl and $(C_1-C_4)$-alkoxy.

In one embodiment of the invention $R^3$ is —$(CH_2)_b$-phenyl, wherein b is 1, 2, 3 or 4 and where phenyl is unsubstituted or substituted as indicated above. In another embodiment of the invention $R^3$ is —$(CH_2)_b$-imidazolyl, —$(CH_2)_b$-triazolyl, —$(CH_2)_b$-Het or —$(CH_2)_b$-pyridinyl, preferably —$(CH_2)_b$-imidazolyl, —$(CH_2)_b$-triazolyl or —$(CH_2)_b$-pyridinyl, more preferably —$(CH_2)_b$-imidazolyl or —$(CH_2)_b$-pyridinyl, wherein b is 1, 2, 3 or 4, preferably 2, 3 or 4, and wherein imidazolyl, triazolyl, Het and pyridinyl are unsubstituted or substituted as indicated above. Examples of groups $R^3$ are 3-(imidazolyl)propyl including 3-(1H-imidazol-1-yl)propyl, 2-(pyridinyl)ethyl and 3-(pyridinyl)propyl including 2-(pyridin-3-yl)ethyl, 2-(pyridin-4-yl)ethyl, 3-(pyridin-3-yl)propyl and 3-(pyridin-4-yl)propyl, and 3-(triazolyl)propyl including 3-(1H-1,2,3-triazol-1-yl) propyl and 3-(1H-1,2,4-triazol-1-yl)propyl. In one embodiment of the invention an imidazolyl group or triazolyl groups present in the group $R^3$ is bonded via a ring nitrogen atom and is, for example, 1H-imidazol-1-yl or 1H-triazol-1-yl. In another embodiment of the invention an imidazolyl group or triazolyl groups present in the group $R^3$ is bonded via a ring carbon atom and is, for example, 1H-imidazol-4-yl or 1H-1,2,4-triazol-3-yl.

Substituted phenyl, imidazolyl, triazolyl and pyridinyl groups present in the group $R^3$ are preferably substituted by one or more, for example one or two, identical or different substituents selected from the group consisting of fluorine, chlorine, bromine, $(C_1-C_4)$-alkyl, trifluoromethyl, $(C_1-C_4)$-alkoxy and trifluoromethoxy. Substituted imidazolyl, triazolyl and pyridinyl groups present in the group $R^3$ are more preferably substituted by one or more, for example one or two, identical or different $(C_1-C_4)$-alkyl substituents.

$R^4$ and $R^7$ that are independent of one another and can be identical or different, are preferably selected from the group consisting of hydrogen, $(C_1-C_4)$-alkyl, trifluoromethyl, methoxy, fluorine, chlorine, nitro, —CO—$R^{10}$, —$NR^8R^9$, —NH—CO-methyl, —$SO_2$—$NR^8R^9$, —$SO_2$-methyl and —$SO_2$—$CH_2$-phenyl. Preferably the total number of nitro groups present in a compound of the formula I according to the invention is not greater than two. More preferably $R^4$ and $R^7$ independently of one another are selected from the group consisting of hydrogen, $(C_1-C_4)$-alkyl, trifluoromethyl, methoxy, fluorine and chlorine, particularly preferably from the group consisting of hydrogen and $(C_1-C_4)$-alkyl, for example from the group consisting of hydrogen and methyl.

$R^5$ and $R^6$ which are independent of one another and can be identical or different, are preferably selected from the group consisting of hydrogen, $(C_1-C_4)$-alkyl, trifluoromethyl, methoxy, fluorine, chlorine, nitro, —CO—$R^{10}$, —$NR^8R^9$, —NH—CO-methyl, —$SO_2$—$NR^8R^9$, —$SO_2$-methyl and —$SO_2$—$CH_2$-phenyl, more preferably from the group consisting of hydrogen, $(C_1-C_4)$-alkyl, trifluoromethyl, methoxy, fluorine, chlorine, nitro, —CO—$R^{10}$, —$SO_2$—$NR^8R^9$, —$SO_2$-methyl and —$SO_2$—$CH_2$-phenyl. In one embodiment of the invention $R^4$ is hydrogen, $R^5$ is hydrogen, flourine, chlorine or methyl, in particular hydrogen, A is $CR^6$ wherein $R^6$ is hydrogen, $(C_1-C_4)$-alkyl, trifluoromethyl, methoxy, fluorine, chlorine, nitro, —CO—$R^{10}$, —$SO_2$—$NR^8R^9$, —$SO_2$-methyl or —$SO_2$—$CH_2$-phenyl, in particular trifluoromethyl, fluorine, chlorine or nitro, more particularly trifluoromethyl or nitro, for example nitro, and B is $CR^7$ wherein $R^7$ is hydrogen.

$R^8$ and $R^9$ that are independent of one another and can be identical or different, are preferably selected from the group consisting of hydrogen and $(C_1-C_2)$-alkyl, more preferably from the group consisting of hydrogen and methyl.

$R^{10}$ preferably is hydroxy, $(C_1-C_2)$-alkoxy such as methoxy or ethoxy, or —$NR^8R^9$, more preferably hydroxy or $(C_1-C_2)$-alkoxy such as methoxy or ethoxy.

Het preferably is a residue of a saturated 5-membered or 6-membered monocyclic heterocycle which contains a ring nitrogen atom via which it is bonded, and which additionally can contain a further ring heteroatom selected from the group consisting of N, O and S, and which is unsubstituted or substituted by one or more identical or different substituents selected from the group consisting of $(C_1-C_4)$-alkyl and —$(CH_2)_d$-phenyl wherein d is 0, 1 or 2. More preferably Het is selected from the group consisting of pyrrolidin-1-yl, piperidin-1-yl, morpholin-4-yl, thiomorpholin-4-yl and piperazin-1-yl which are unsubstituted or substituted as indicated before. Particularly preferably Het is pyrrolidin-1-yl or piperidin-1-yl.

Heteroaryl preferably is a residue of an aromatic 5-membered or 6-membered monocyclic heterocycle which contains 1, 2, or 3, preferably 1 or 2, identical or different ring heteroatoms selected from the group consisting of N, O and S. Substituted heteroaryl is preferably substituted by one or more, for example one or two, identical or different substituents selected from the group consisting of fluorine, chlorine, bromine, $(C_1-C_4)$-alkyl, trifluoromethyl, $(C_1-C_4)$-alkoxy and trifluoromethoxy, more preferably by substituents selected from the group consisting of fluorine, chlorine and $(C_1-C_4)$-alkyl.

Preferred compounds according to the invention are those compounds of formula I in which one or more of the groups contained therein have any one of the preferred definitions given above or any one or some of the specific denotations comprised by the definitions of the respective groups, all combinations of preferred definitions and/or specific denotations being a subject of the present invention. With respect to all preferred compounds of the formula I the present invention just so includes all stereoisomeric forms and mixtures thereof in all ratios, and their physiologically acceptable salts.

A group of preferred compounds according to the invention is formed by compounds of the formula I in which simultaneously A is $CR^6$ or N and B is $CR^7$ or N, but A and B are not simultaneously N;

$R^1$ is $(C_1-C_6)$-alkyl that is unsubstituted or substituted by one or more identical or different substituents selected from the group consisting of $(C_3-C_6)$-cycloalkyl, phenyl, biphenylyl, naphthyl, indanyl, thienyl and pyridinyl;

$R^2$ is hydrogen, $(C_1-C_4)$-alkyl, trifluoromethyl, —$(CH_2)_a$-$(C_3-C_6)$-cycloalkyl, —$(CH_2)_a$-phenyl, —$(CH_2)_a$-imidazolyl or —$(CH_2)_a$-pyridinyl, wherein a is 0 or 1;

$R^3$ is —$(CH_2)_b$-phenyl, —$(CH_2)_b$-imidazolyl, —$(CH_2)_b$-triazolyl, —$(CH_2)_b$-Het or —$(CH_2)_b$-pyridinyl, wherein b is 1, 2, 3 or 4;

$R^4$, $R^5$, $R^6$ and $R^7$ that are independent of one another and can be identical or different, are selected from the group consisting of hydrogen, $(C_1-C_4)$-alkyl, trifluoromethyl, methoxy, fluorine, chlorine, nitro, —CO—$R^{10}$, —$NR^8R^9$, —NH—CO-methyl, —$SO_2$—$NR^8R^9$, —$SO_2$-methyl and —$SO_2$—$CH_2$-phenyl;

$R^8$ and $R^9$ that are independent of one another and can be identical or different, are selected from the group consisting of hydrogen and methyl;

$R^{10}$ is hydroxy, $(C_1-C_2)$-alkoxy or $-NR^8R^9$,

Het is a residue of a saturated 5-membered or 6-membered monocyclic heterocycle which contains a ring nitrogen atom via which it is bonded, and which additionally can contain a further ring heteroatom selected from the group consisting of N, O and S, and which is unsubstituted or substituted by one or more identical or different substituents selected from the group consisting of $(C_1-C_4)$-alkyl and $-(CH_2)_d$-phenyl, wherein d is 0, 1 or 2;

where all residues phenyl, biphenylyl, naphthyl, indanyl, thienyl, pyridinyl, imidazolyl and triazolyl in each case are unsubstituted or are independently of one another substituted by one or more identical or different substituents selected from the group consisting of fluorine, chlorine, bromine, cyano, $(C_1-C_4)$-alkyl, trifluoromethyl, $(C_1-C_4)$-alkoxy and trifluoromethoxy;

in all their stereroisomeric forms and mixtures thereof in any ratio, and their physiologically acceptable salts;

provided that $R^3$ cannot be unsubstituted $-CH_2$-phenyl when simultaneously A and B are CH, $R^1$ and $R^2$ are methyl, and $R^4$ and $R^5$ are hydrogen.

A group of particularly preferred compounds according to the invention is formed by compounds of the formula I in which simultaneously A is $CR^6$ or N and B is $CR^7$ or N, but A and B are not simultaneously N;

$R^1$ is $(C_1-C_6)$-alkyl that is substituted by unsubsutituted phenyl or by phenyl which is substituted by one or more identical or different substituents selected from the group consisting of fluorine, chlorine, bromine, cyano, $(C_1-C_4)$-alkyl, trifluoromethyl, $(C_1-C_4)$-alkoxy and trifluoromethoxy;

$R^2$ is hydrogen, $(C_1-C_4)$-alkyl, trifluoromethyl or $(C_3-C_6)$-cycloalkyl;

$R^3$ is $-(CH_2)_b$-imidazolyl, $-(CH_2)_b$-triazolyl or $-(CH_2)_b$-pyridinyl, wherein b is 1, 2, 3 or 4, and wherein imidazolyl, triazolyl and pyridinyl are all unsubstituted or substituted by one or more identical or different $(C_1-C_4)$-alkyl substituents;

$R^4$ and $R^7$ that are independent of one another and can be identical or different, are selected from the group consisting of hydrogen, $(C_1-C_4)$-alkyl, trifluoromethyl, methoxy, fluorine and chlorine;

$R^5$ and $R^6$ that are independent of one another and can be identical or different, are selected from the group consisting of hydrogen, $(C_1-C_4)$-alkyl, trifluoromethyl, methoxy, fluorine, chlorine, nitro, $-CO-R^{10}$, $-NR^8R^9$, $-NH-CO$-methyl, $-SO_2-NR^8R^9$, $-SO_2$-methyl and $-SO_2-CH_2$-phenyl; $R^8$ and $R^9$ that are independent of one another and can be identical or different, are selected from the group consisting of hydrogen and methyl;

$R^{10}$ is hydroxy, $(C_1-C_2)$-alkoxy or $-NR^8R^9$, in all their stereroisomeric forms and mixtures thereof in any ratio, and their physiologically acceptable salts.

The invention also encompasses all combinations of particular and preferred aspects of the invention noted herein.

A further subject of the present invention are processes of preparation by which the compounds of the formula I are obtainable. According to one such process, the compounds of formula I can be prepared, for example, from the amino-substituted carboxylic acids of formula IV and the acetals of formula V.

As starting compounds for the synthesis of compounds of the formula I halogen-substituted aromatic nitrites, i.e. benzonitriles or pyridinecarbonitriles, of the formula II can be employed in which A, B, $R^4$ and $R^5$ have the meanings indicated above with respect to the compounds of formula I or else functional groups can also be present in protected form or in the form of precursor groups. Hal in formula II denotes halogen, preferably bromine. The nitrites of the formula II can be obtained by standard procedures from the respective carboxylic acids, i.e. the compounds for formula II which contain a carboxy group COOH instead of the cyano group CN, for example by conversion of the carboxylic acid moiety into the carboxylic acid chloride by means of thionyl chloride or oxalyl chloride in an inert solvent such as toluene or a chlorinated hydrocarbon and subsequent treatment of the obtained acid chloride with sulfamide in a suitable inert solvent at elevated temperature, for example in sulfolane at temperatures from about 100° C. to about 160° C.

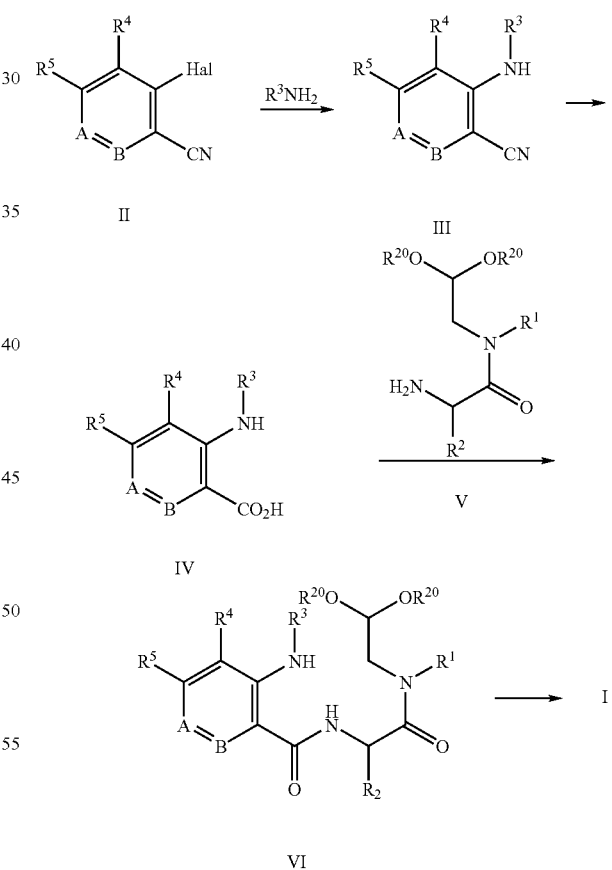

The halogen-substituted nitrites of the formula II can be employed into a cross-coupling reaction with primary amines of the formula $R^3-NH_2$ in which $R^3$ has the meanings indicated above with respect to the compounds of formula I. The reaction can be performed, for example, in an inert solvent such as an ether like tetrahydrofuran or dioxane, at temperatures from about 40° C. to about 80° C. in the presence of a suitable transition metal catalyst and a suitable base. Suitable bases include, for example, alkali metal ($C_1$–$C_4$)-alkoxides such as sodium and potassium tert-butoxide. Suitable catalysts include, for example, palladium catalysts. Particularly favorably the reaction is performed in the presence of 1,1'-bis(diphenylphosphino)-ferrocene palladium dichloride (Pd(dppf)Cl$_2$) which is preferably used in an amount of from about 2 mol-% to about 10 mol-%, for example about 5 mol-%, preferably in the presence of an additional amount, for example from about 5 mol-% to about 30 mol-% such as about 15 mol-%, of the ligand 1,1'-bis (diphenylphosphino)ferrocene (cf. Driver and Hartwig, J. Am. Chem. Soc. 118 (1996) 7217). The obtained amino-substituted nitrile of the formula II, in which A, B, $R^4$ and $R^5$ have the meanings indicated above with respect to the compounds of formula II and $R^3$ has the meanings indicated above with respect to the compounds of formula I, is then hydrolyzed to the carboxylic acid of the formula IV by a standard procedure, for example by treatment with a base like an alkali metal hydroxide such as sodium hydroxide, in the presence of water in a suitable solvent like a ($C_1$–$C_4$)-alkanol such as methanol or ethanol or an ether such as tetrahydrofuran or dioxane, at temperatures from about 40° C. to about 100° C.

The obtained carboxylic acid of the formula IV is coupled under standard conditions for the formation of amide bonds with an amine of the formula V to give a compound of the formula VI. In the compounds of formula V the groups $R^1$ and $R^2$ have the meanings indicated above with respect to the compounds of formula I, and the groups $R^{20}$ in the acetal moiety ($R^{20}O$)$_2$CH— are, for example, ($C_1$–$C_4$)-alkyl groups such as ethyl groups. For the formation of the amide bond the carboxylic acid can be activated, for example, by means of a customary activating agent such as a carbodiimide, for example, N,N'-dicyclohexylcarbodiimide (DCC) or N,N'-diisopropylcarbodiimide (DIC), or O-((cyano (ethoxycarbonyl)methylene)amino)-1,1,3,3-tetramethyluronium tetrafluoroborate (TOTU), in an inert solvent such as an ether like tetrahydrofuran or dioxane or an amide like dimethylformamide or N-methyl-2-pyrrolidone.

The compounds of the formula V can be prepared, for example, by a process which comprises a reductive alkylation. First an aminoacetaldehyde acetal of the formula ($R^{20}O$)$_2$CH—CH$_2$—NH$_2$ is reacted with an aldehyde in the presence of an acid such as p-toluenesulfonic acid under standard conditions to form an intermediary imine the C═N double bond of which is reduced, for example with a complex hydride reducing agent such as sodium borohydride in an alcohol such as methanol, to give the amine of the formula ($R^{20}O$)$_2$CH—CH$_2$—NHR$^1$. In the amine of the formula of the formula ($R^{20}O$)$_2$CH—CH$_2$—NHR$^1$ the groups $R^1$ and $R^{20}$ are defined as indicated above with respect to the compounds of formula V. Said amine is subsequently coupled with an N-protected amino acid of the formula PG-NH—CHR$^2$—COOH in which $R^2$ is defined as indicated above with respect to the compounds of formula I and PG is an amino protecting group, for example the fluoren-9-ylmethoxycarbonyl (Fmoc) protecting group or the benzyloxycarbonylamino (Z) protecting group, the coupling reaction being carried out under standard conditions, for example by means of an activating agent such as a carbodiimide like DCC in an inert solvent such as an ether like tetrahydrofuran. Removal of the protecting group PG under standard conditions, for example by treatment with piperidine or by catalytic hydrogenation, then leads to the compound of formula V.

The final conversion of the compounds of the formula VI in which A, B, $R^1$ to $R^5$ and $R^{20}$ are defined as indicated above with respect to the compounds of formula II and V, to the compounds of the formula I is favorably carried out by treatment with an acid such as formic acid, for example at a temperature from about 10° C. to about 30° C., such as at room temperature, for 1 to 12 hours (cf. Vojkovsky et al., J. Org. Chem. 63 (1998) 3162). If desired, the obtained compounds of formula I, as well as any intermediate compounds, can be purified by customary purification procedures, for example by recrystallization or chromatography.

Another process for the preparation of compounds of the formula I which is favorably performed by applying solid phase techniques, starts with the attachment of a bromoacetaldehyde acetal of formula VII in which $R^{20}$ is defined as indicated above with respect to the compounds of the formula V, to a suitable resin for solid phase synthesis by transacetalization in the presence of an acidic catalyst under standard conditions. I.e., in this starting step an —OR$^{20}$ group in the compound of the formula VII is replaced with an —O—SP group in which SP denotes the solid phase resin including the linking groups. A suitable solid phase resin SP—OH is, for example, ®TentaGel resin in the hydroxy form.

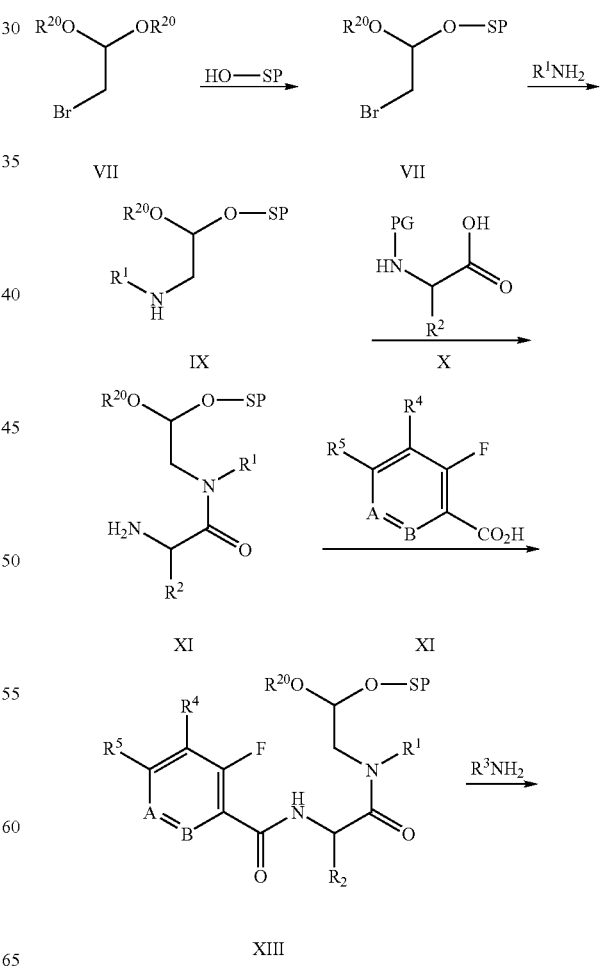

-continued

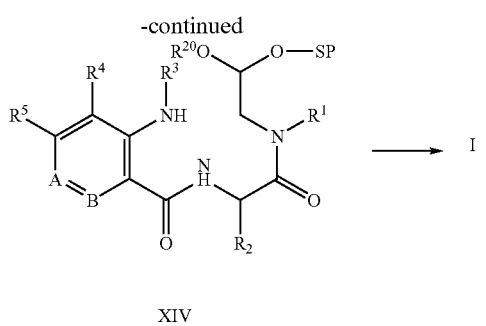

XIV

The obtained resin-bound compound of the formula VIII is then reacted with an amine of the formula $R^1$—$NH_2$ in which $R^1$ is defined as indicated above with respect to the compounds of formula I, for example by shaking the resin with an excess of the amine in an inert solvent such as dimethylsulfoxide. Subsequently, the obtained compound of the formula IX is coupled under standard conditions for the formation of amide bonds with an N-protected amino acid of the formula X in which $R^2$ is defined as indicated above with respect to the compounds of formula I and PG is an amino protecting group, for example the above-mentioned Fmoc or Z protecting groups. As a favorable activating agent for accomplishing the condensation of the compounds of formula IX and X, besides the above-mentioned activating agents for carbocylic acids, tetramethylfluoroformamidinium hexafluorophosphate may be mentioned which can be employed in an inert solvent such as dimethylformamide in the presence of a tertiary amine such as ethyldiisopropylamine at room temperature. After removal of the protecting group PG, for example by means of piperidine in the case of the Fmoc protecting group, the obtained compound of the formula XI is reacted in another coupling reaction with a suitable fluoro-substituted benzoic acid or pyridinecarboxylic acid, respectively, of the formula XII in which A, B, $R^4$ and $R^5$ are defined as indicated above with respect to the compounds of formula II, for example by means of an carbodiimide like DIC in an inert solvent such as dimethylformamide with addition of N-hydroxybenzotriazole. In the obtained compound of the formula XIII an activated fluorine atom can then be replaced in a nucleophilic substitution reaction with the group —$NHR^3$ by treatment with an amine of the formula $R^3$—$NH_2$ in which $R^3$ is defined as indicated above with respect to the compounds of formula I, for example by shaking the resin with an excess of the amine in an inert solvent such dimethylsulfoxide. Finally, the obtained compound of the formula XIV is simultaneously cleaved from the resin and converted into the compound of the formula I by treatment with an acid such as formic acid at room temperature. In the compounds of formulae XIII and XIV, A, B, $R^4$ and $R^5$ are defined as indicated above with respect to the compounds of formula XII, $R^1$ and $R^2$ are defined as indicated above with respect to the compounds of formula XI and $R^3$ is defined as indicated above with respect to the compounds of formula I.

All reactions used for the above-described syntheses of the compounds of the formula I are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a compound of the formula I, it can generally be necessary or advantageous to temporarily block functional groups by introducing protective groups and deprotect them at a later stage of the synthesis, or introduce functional groups in the form of precursor groups which later are converted into the desired functional groups. As an example of a precursor group the nitro group may be mentioned which can be converted into an amino group by reduction, for example by catalytic hydrogenation. Such synthesis strategies, and protective groups and precursor groups that are suitable in a specific case, are known to the skilled person.

The compounds according of the formula I are useful pharmacologically active compounds which upregulate the expression of endothelial NO synthase and can be employed as medicaments for the treatment of various diseases. In the context of the present invention, treatment is understood as comprising both therapy, including alleviation and cure, of disease symptoms and prevention or prophylaxis of disease symptoms, such as, for example, the prevention of the appearance of asthmatic disease symptoms or the prevention of myocardial infarction or of myocardial reinfarction in relevant patients. The diseases or disease symptoms can be acute or chronic. Diseases which can be treated with the compounds of the formula I include, for example, cardiovascular diseases like stable and unstable angina pectoris, coronary heart disease, Prinzmetal angina (spasm), acute coronary syndrome, heart failure, myocardial infarction, stroke, thrombosis, peripheral artery occlusive disease (PAOD), endothelial dysfunction, atherosclerosis, restenosis, endothel damage after PTCA, hypertension including essential hypertension, pulmonary hypertension and secondary hypertension (renovascular hypertension, chronic glomerulonephritis), erectile dysfunction, and ventricular arrhythmia. Further, the compounds of the formula I lower the cardiovascular risk of postmenopausal women or after intake of contraceptives. Compounds of the formula I can additionally be used in the treatment, i.e. the therapy and prevention, of diabetes and diabetes complications (nephropathy, retinopathy), angiogenesis, asthma bronchiale, chronic renal failure, cirrhosis of the liver, osteoporosis, restricted memory performance or a restricted ability to learn. Preferred indications are stable angina pectoris, coronary heart disease, hypertension, endothelial dysfunction, atherosclerosis and diabetes complications.

The compounds of the formula I can be used in combination with other pharmacologically active compounds or pharmaceuticals, preferably with compounds which are able to enhance the effect of the compounds according to the formula I. Examples of such other compounds include statins; ACE inhibitors; AT1 antagonists; argininase inhibitors; PDE V inhibitors; calcium antagonists; alpha blockers; beta blockers; metimazol and analogous compounds; arginine; tetrahydrobiopterin; vitamins, in particular vitamin C and vitamin B6; niacine.

The compounds of the formula I and their physiologically acceptable salts, optionally in combination with other pharmacologically active compounds, can be administered to animals, preferably to mammals, and in particular to humans, as pharmaceuticals by themselves, in mixtures with one another or in the form of pharmaceutical preparations. Further subjects of the present invention therefore also are the compounds of the formula I and their physiologically acceptable salts for use as pharmaceuticals, their use as transcription stimulating agents or upregulating agents of endothelial NO synthase, for example in conditions in which an increased expression of said enzyme or an increased NO level or the normalization of a decreased NO level in a patient is desired, and in particular their use in the treatment, i.e. the therapy and prevention, of the above-mentioned diseases or syndromes, as well as their use for preparing medicaments for these purposes. Furthermore, a subject of the present invention are pharmaceutical preparations (or pharmaceutical compositions) which comprise an effective dose of at least one compound of the formula I and/or a physiologically acceptable salt thereof and a pharmaceutically acceptable carrier, i.e. one or more pharmaceutically acceptable carrier substances and/or additives. A subject of the present invention also is the use of the compound of the formula I, in which simultaneously A and B are CH, $R^1$ and $R^2$ are methyl, $R^4$ and $R^5$ are hydrogen, and $R^3$ is unsubstituted —$CH_2$-phenyl, which compound is excluded from the above-defined compounds which are a subject of the present invention per se, and physiologically acceptable salt thereof, as a pharmaceutical, its use as transcription stimulating agent or upregulating agent of endothelial NO synthase, its use in the treatment of the above-mentioned diseases or syndromes, and pharmaceutical preparations which comprise an effective dose of said compound and/or a physiologically acceptable salt thereof and a pharmaceutically acceptable carrier. All explanations above and below relating to the use of compounds of the formula I also apply to said compound in which simultaneously A and B are CH, $R^1$ and $R^2$ are methyl, $R^4$ and $R^5$ are hydrogen, and $R^3$ is unsubstituted —$CH_2$-phenyl, and its physiologically acceptable salts.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously, for example in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, among others, on the disease to be treated and on its severity.

The amount of a compound of the formula I and/or its physiologically acceptable salts in the pharmaceutical preparations normally ranges from about 0.2 to about 800 mg, preferably from about 0.5 to about 500 mg, in particular from about 1 to about 200 mg, per dose, but depending on the type of the pharmaceutical preparation it may also be higher. The pharmaceutical preparations usually comprise from about 0.5 to about 90 percent by weight of the compounds of the formula I and/or their physiologically acceptable salts. The production of the pharmaceutical preparations can be carried out in a manner known per se. To this end, one or more compounds of the formula I and/or their physiologically acceptable salts together with one or more solid or liquid pharmaceutical carrier substances (or vehicles) and/or additives (or auxiliary substances) and, if a combination preparation is desired, other physiologically active compounds having therapeutic or prophylactic action are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, starch derivatives, talc, stearic acid or its salts, etc. Soft gelatin capsules and suppositories can comprise, for example, fats, waxes, semi-solid and liquid polyols, natural or hardened oils, etc. Suitable carrier substances for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formula I or their physiologically acceptable salts and to use the resulting lyophilisates, for example, for preparing preparations for injection or infusion. Suitable carriers for microcapsules, implants or rods are, for example, copolymers of glycolic acid and lactic acid. Besides the compound or compounds according to the invention and carrier substances, the pharmaceutical preparations can also contain additives such as, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formula I to be administered and/or of a physiologically acceptable salt thereof depends on the individual case and, as is customary, has to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the use is for the therapy of a acute or chronic disease or prophylactic, or on whether other active compounds are administered in addition to compounds of the formula I. In general, a daily dose of from about 0.01 mg/kg to about 100 mg/kg, preferably from about 0.1 mg/kg to about 10 mg/kg, in particular from about 0.3 mg/kg to about 5 mg/kg (in each case mg per kg of bodyweight) is appropriate for administration to an adult weighing about 75 kg in order to obtain the desired results. The daily dose can be administered in a single dose or, in particular when larger amounts are administered, divided into several, for example two, three or four individual doses.

In some cases, depending on the individual response, it may be necessary to deviate upwards or downwards from the given daily dose.

The compounds of the formula I can also be used for other purposes than those indicated in the foregoing. Non-limiting examples include the use as diagnostics, for example the use in methods for determining the activity of endothelial NO synthase in biological samples, the use as biochemical tools and the use as intermediates for the preparation of further compounds, for example pharmacologically active compounds.

EXAMPLES

Basic compounds that were purified by preparative HPLC using an eluent that contained trifluoroacetic acid, were obtained in the form of acid addition salts with trifluoroacetic acid. The compounds were characterized by analytical high pressure liquid chromatography (HPLC) and/or mass spectrometry (MS) and/or nuclear magnetic resonance spectrometry (NMR). The MS data given below were obtained by electron spray ionization (ESI). The analytical HPLC conditions were as follows.

Method HPLC A: An Agilent 1100 LC/MSD device with a diode array UV detector operated at 220 nm was used. The column used was a Merck Purospher RP18, 5 µm, 2×55 mm, column. The flow rate was 0.5 ml/min. Eluent A1: acetonitrile (with 0.05 vol-% of trifluoroacetic acid). Eluent A2: water (with 0.05 vol-% of trifluoroacetic acid). Gradient: From 5% A1+95% A2 to 95% A1+5% A2 in 4 min.

Method HPLC B: A Shimadzu LC-10A HPLC device with a diode array UV detector operated at 220 nm and a Perkin-Elmer Sciex, single quadrupole API 150EX Mass Chrom 1.1 MS device were used. The column used was a Keystone Scientific, Inc., SCL-10A, RP18, 20×2 mm, column. The flow rate was 0.7 ml/min. Eluent B1: acetonitrile (with 0.1 vol-% of trifluoroacetic acid). Eluent B2: water (with 0.1 vol-% of trifluoroacetic acid). Gradient: From 2% B1+98% B2 to 85% B1+15% B2 in 3 min, then to 100% B1+0% B2 in 0.1 min.

Example 1

(4S)-9-(3-(Imidazol-1-yl)propyl)-4-isopropyl-6-nitro-2-(4-phenylbutyl)-1,2,9,9a-tetrahydro-2,4a,9-triaza-anthracene-3,10(4H)-dione trifluoroacetic acid salt

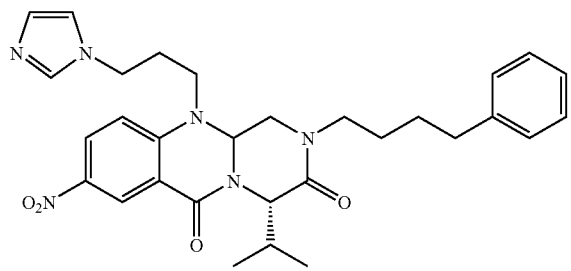

®TentaGel resin was suspended in 1,2-dichloroethane, 1 equivalent of quinolinium toluenesulfonate was added, and the mixture was heated to reflux. 4 equivalents of 2-bromo-1,1-diethoxyethane were added, and the mixture was heated under reflux for 4 hours while distilling off ethanol. The resin was separated, washed with dimethylformamide and dioxane and lyophilized. The resin was shaken in dimethylsulfoxide with an excess of 4-phenylbutylamine at 60° C. for 14 hours. The resin was separated and washed with dimethylformamide, methanol and dichloromethane. The resin was shaken in dimethylformamide with 3 equivalents of Fmoc-L-valine, 3 equivalents of tetramethylfluoroformamidium hexafluorophosphate (TFFH) and 6 equivalents of ethyldiisopropylamine at room temperature for two days. The resin was separated, washed with dichloromethane and dimethylformamide, and the Fmoc protecting group was cleaved off by treatment with an excess of a 20% solution of piperidine in dimethylformamide. The resin was separated, washed, and shaken in dimethylformamide with 3 equivalents of 2-fluoro-5-nitrobenzoic acid, 3 equivalents of diisopropylcarbodiimide (DIC) and 3 equivalents of N-hydroxybenzotriazole (HOBT) for 16 hours at room temperature. The resin was separated, washed with dimethylformamide, dichloromethane and methanol, and shaken in dimethylsulfoxide with 15 equivalents of 3-(imidazol-1-yl)propylamine at room temperature for 16 hours. The resin was separated and washed with dimethylformamide and dichloromethane. Finally, cleavage of the prepared compound from the resin and N-acyliminium ion cyclization were effected by treatment with formic acid at room temperature for 3 to 4 hours. The crude product was purified by preparative HPLC (acetonitrile/water/trifluoroacetic acid).

MS: m/e=545 (M+H)$^+$. Retention time (HPLC A): 4.29 min.

Example 2

(4S)-2-(4-tert-Butylbenzyl)-9-(3-(imidazol-1-yl)propyl)-4-isopropyl-6-nitro-1,2,9,9a-tetrahydro-2,4a,9-triaza-anthracene-3,10(4H)-dione trifluoroacetic acid salt

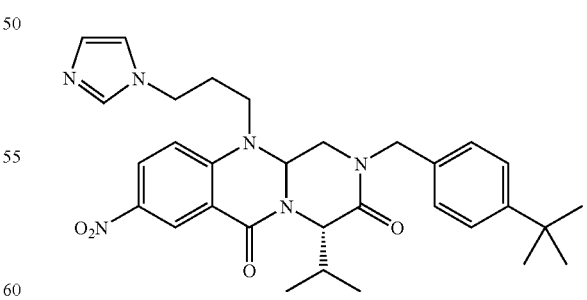

The title compound was prepared according to the procedure described in example 1, using 4-tert-butylbenzylamine instead of 4-phenylbutylamine.

MS: m/e=559 (M+H)$^+$. Retention time (HPLC B): 6.50 min.

Example 3

(4S)-9-(3-(Imidazol-1-yl)propyl)-4-isopropyl-2-(naphth-1-ylmethyl)-6-nitro-1,2,9,9a-tetrahydro-2,4a,9-triaza-anthracene-3,10(4H)-dione trifluoroacetic acid salt

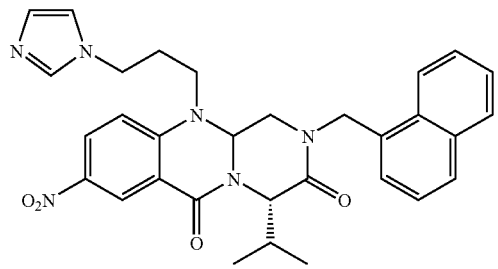

The title compound was prepared according to the procedure described in example 1, using naphth-1-ylmethylamine instead of 4-phenylbutylamine.

MS: m/e=553 (M+H)$^+$. Retention time (HPLC B): 5.88 min.

Example 4

(4S)-4-(3-Fluorobenzyl)-9-(3-(imidazol-1-yl)propyl)-6-nitro-2-(4-phenylbutyl)-1,2,9,9a-tetrahydro-2,4a,9-triaza-anthracene-3,10(4H)-dione trifluoroacetic acid salt

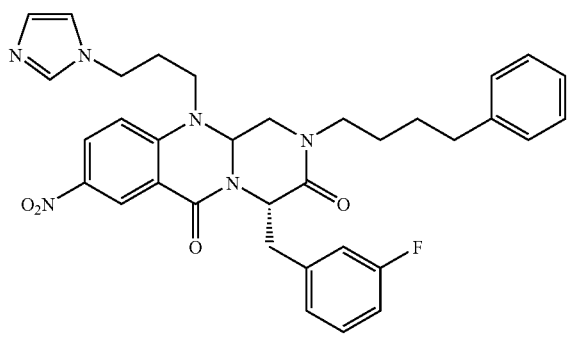

The title compound was prepared according to the procedure described in example 1, using (S)-2-(9H-fluoren-9-ylmethoxycarbonylamino)-3-(3-fluorophenyl)propionic acid instead of Fmoc-L-valine.

MS: m/e=611 (M+H)$^+$. Retention time (HPLC B): 6.46 min.

Example 5

(4S)-4-Cyclohexyl-9-(3-(imidazol-1-yl)propyl)-6-nitro-2-(4-phenylbutyl)-1,2,9,9a-tetrahydro-2,4a,9-triaza-anthracene-3,10(4H)-dione trifluoroacetic acid salt

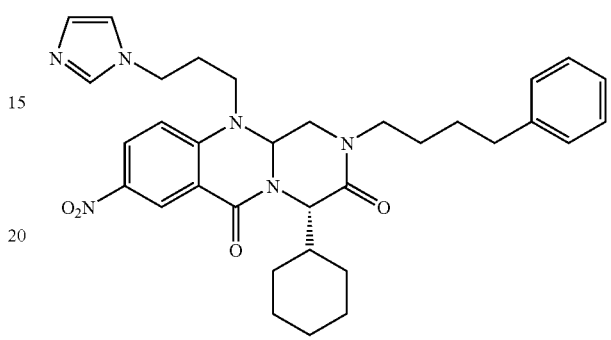

The title compound was prepared according to the procedure described in example 1, using (S)-cyclohexyl-(9H-fluoren-9-ylmethoxycarbonylamino)acetic acid instead of Fmoc-L-valine.

MS: m/e=585 (M+H)$^+$. Retention time (HPLC B): 6.54 min.

Example 6

(4S)-4-(3,4-Dimethoxybenzyl)-9-(3-(imidazol-1-yl)propyl)-6-nitro-2-(4-phenylbutyl)-1,2,9,9a-tetrahydro-2,4a,9-triaza-anthracene-3,10(4H)-dione trifluoroacetic acid salt

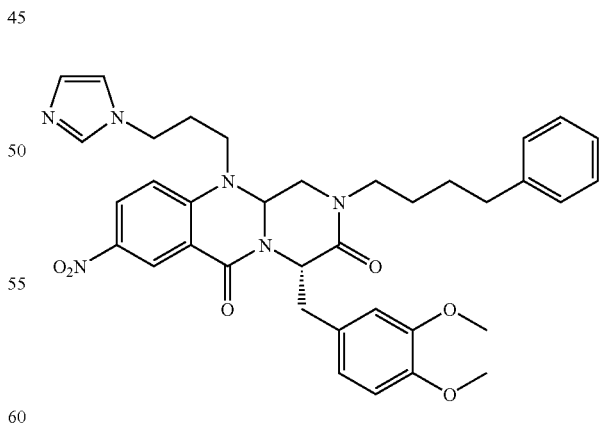

The title compound was prepared as described in example 1, using (S)-3-(3,4-dimethoxyphenyl)-2-(9H-fluoren-9-ylmethoxycarbonylamino)propionic acid instead of Fmoc-L-valine.

MS: m/e=653 (M+H)$^+$. Retention time (HPLC B): 6.04 min.

Example 7

(4S)-4-Isopropyl-6-nitro-2-(4-phenylbutyl)-9-(2-(pyridin-4-yl)ethyl)-1,2,9,9a-tetrahydro-2,4a,9-triaza-anthracene-3,10(4H)-dione trifluoroacetic acid salt

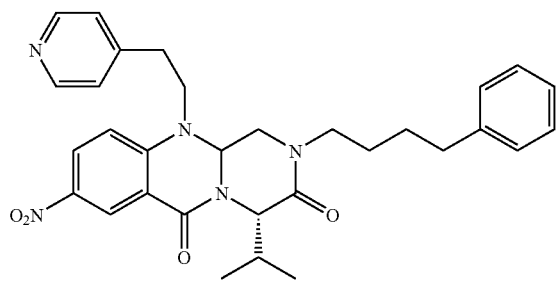

The title compound was prepared according to the procedure described in example 1, using 2-(pyridin-4-yl)ethylamine instead of 3-(imidazol-1-yl)propylamin.

MS: m/e=542 (M+H)⁺. Retention time (HPLC B): 6.00 min.

Example 8

(4S)-4-(1H—Imidazol-4-ylmethyl)-6-nitro-2,9-bis(4-phenylbutyl)-1,2,9,9a-tetrahydro-2,4a,9-triaza-anthracene-3,10(4H)-dione trifluoroacetic acid salt

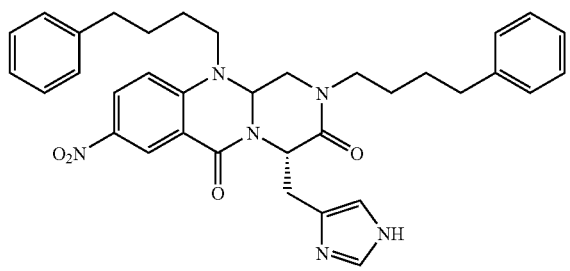

The title compound was prepared according to the procedure described in example 1, using (S)-2-(9H-fluoren-9-ylmethoxycarbonylamino)-3-(1H-imidazol-4-yl)propionic acid instead of Fmoc-L-valine and 4-phenylbutylamine instead of 3-(imidazol-1-yl)propylamin.

MS: m/e=607 (M+H)⁺. Retention time (HPLC B): 7.36 min.

Example 9

(4S)-4-(1H-Imidazol-4-ylmethyl)-6-nitro-2-(4-phenylbutyl)-9-(4-trifluoromethoxy-benzyl)-1,2,9,9a-tetrahydro-2,4a,9-triaza-anthracene-3,10(4H)-dione trifluoroacetic acid salt

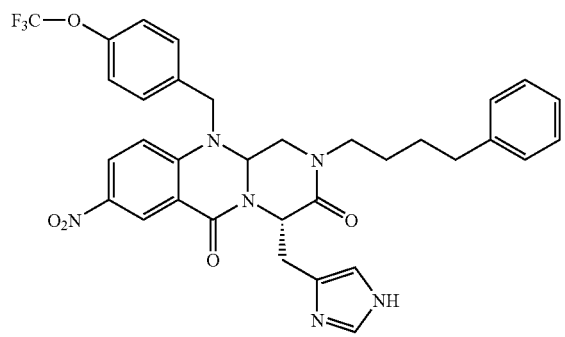

The title compound was prepared according to the procedure described in example 1, using (S)-2-(9H-fluoren-9-ylmethoxycarbonylamino)-3-(1H-imidazol-4-yl)propionic acid instead of Fmoc-L-valine and 4-trifluoromethoxybenzylamine instead of 3-(imidazol-1-yl)propylamin.

MS: m/e=649 (M+H)⁺. Retention time (HPLC B): 7.25 min.

Example 10

(4S)-9-(3-(Imidazol-1-yl)propyl)-4-isopropyl-2-(4-phenyl butyl)-6-trifluoromethyl-1,2,9,9a-tetrahydro-2,4a,9-triaza-anthracene-3,10(4H)-dione trifluoroacetic acid salt

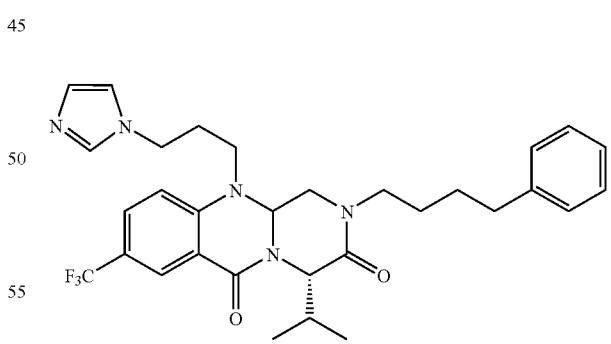

The title compound was prepared according to the procedure described in example 1, using 2-fluoro-5-trifluoromethylbenzoic acid instead of 2-fluoro-5-nitrobenzoic acid.

MS: m/e=514 (M+H)⁺. Retention time (HPLC B): 5.41 min.

Example 11

(4S)-9-(3-(Imidazol-1-yl)propyl)-4-isopropyl-6-trifluoromethyl-2-(4-trifluoromethyl-benzyl)-1,2,9,9a-tetrahydro-2,4a,9-triaza-anthracene-3,10(4H)-dione trifluoroacetic acid salt

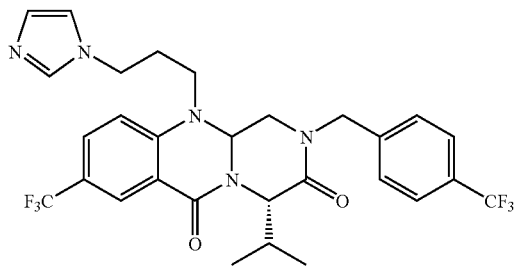

The title compound was prepared according to the procedure described in example 1, using 2-fluoro-5-trifluoromethylbenzoic acid instead of 2-fluoro-5-nitrobenzoic acid and 4-trifluoromethylbenzylamine instead of 4-phenylbutylamine.

MS: m/e=594 (M+H)$^+$. Retention time (HPLC B): 5.38 min.

Example 12

(4S)-4-Isopropyl-9-(2-(pyridin-4-yl)ethyl)-6-trifluoromethyl-2-(4-trifluoromethyl benzyl)-1,2,9,9a-tetrahydro-2,4a,9-triaza-anthracene-3,10(4H)-dione trifluoroacetic acid salt

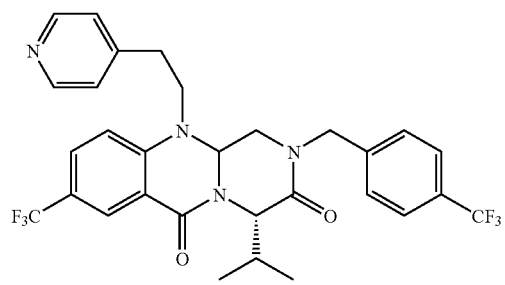

The title compound was prepared according to the procedure described in example 1, using 2-fluoro-5-trifluoromethylbenzoic acid instead of 2-fluoro-5-nitrobenzoic acid, 4-trifluoromethylbenzylamine instead of 4-phenylbutylamine and 2-(pyridin-4-yl)ethylamine instead of 3-(imidazol-1-yl)propylamine.

MS: m/e=591 (M+H)$^+$. Retention time (HPLC B): 5.37 min.

Example 13

(4S)-4-Cyclohexyl-9-(3-(imidazol-1-yl)propyl)-2-(4-phenylbutyl)-6-trifluoromethyl-1,2,9,9a-tetrahydro-2,4a,9-triaza-anthracene-3,10(4H)-dione trifluoroacetic acid salt

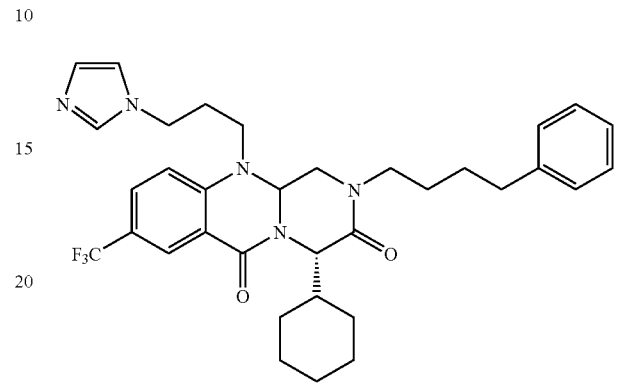

The title compound was prepared according to the procedure described in example 1, using 2-fluoro-5-trifluoromethylbenzoic acid instead of 2-fluoro-5-nitrobenzoic acid and (S)-cyclohexyl-(9H-fluorenyl-9-ylmethoxycarbonylamino)acetic acid instead of Fmoc-L-valine.

MS: m/e=608 (M+H)$^+$. Retention time (HPLC B): 5.73 min.

Example 14

(4S)-2-(2,4-Dimethoxybenzyl)-9-(3-(imidazol-1-yl)propyl)-4-isopropyl-6-trifluoromethyl-1,2,9,9a-tetrahydro-2,4a,9-triaza-anthracene-3,10(4H)-dione trifluoroacetic acid salt

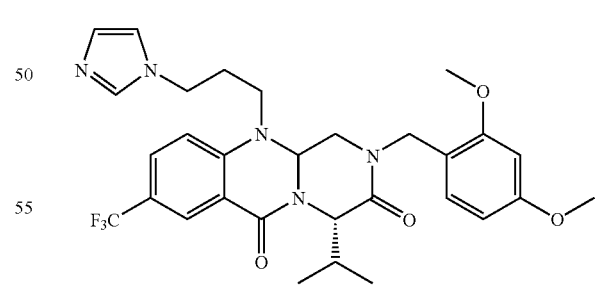

The title compound was prepared according to the procedure described in example 1, using 2-fluoro-5-trifluoromethylbenzoic acid instead of 2-fluoro-5-nitrobenzoic acid and 2,4-dimethoxybenzylamine instead of 4-phenylbutylamine.

MS: m/e=586 (M+H)$^+$. Retention time (HPLC B): 4.94 min.

Example 15

(4S)-2-(4-tert-Butylbenzyl)-9-(3-(imidazol-1-yl)propyl)-4-isopropyl-6-trifluoromethyl-1,2,9,9a-tetrahydro-2,4a,9-triaza-anthracene-3,10(4H)-dione trifluoroacetic acid salt

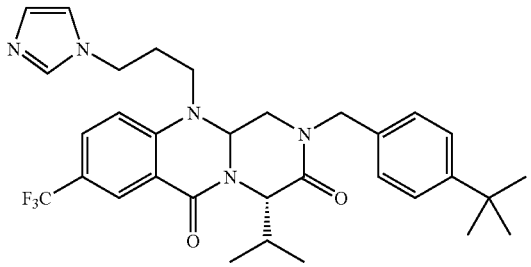

The title compound was prepared according to the procedure described in example 1, using 2-fluoro-5-trifluoromethylbenzoic acid instead of 2-fluoro-5-nitrobenzoic acid and 4-tert-butylbenzylamine instead of 4-phenylbutylamine.

MS: m/e=582 (M+H)$^+$. Retention time (HPLC B): 5.70 min.

Example 16

(4S)-4-(3-Fluorobenzyl)-9-(3-(imidazol-1-yl)propyl)-2-(4-phenylbutyl)-6-trifluoromethyl-1,2,9,9a-tetrahydro-2,4a,9-triaza-anthracene-3,10(4H)-dione trifluoroacetic acid salt

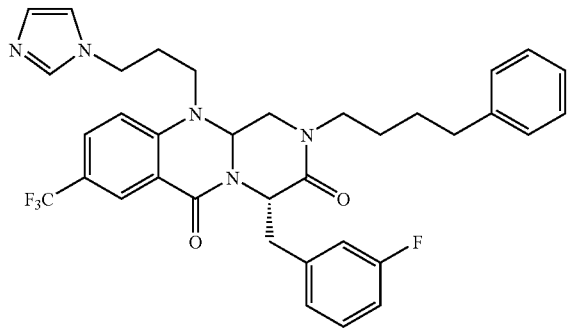

The title compound was prepared according to the procedure described in example 1, using 2-fluoro-5-trifluoromethylbenzoic acid instead of 2-fluoro-5-nitrobenzoic acid and (S)-2-(9H-fluorenyl-9-ylmethoxycarbonylamino)-3-(3-fluorophenyl)propionic acid instead of Fmoc-L-valine.

MS: m/e=634 (M+H)$^+$. Retention time (HPLC B): 5.66 min.

General Procedure A for the Preparation of Compounds of the Formula I by Solution Chemistry a) For the preparation of the substituted amino acid amide of formula V the respective aldehyde, for example 4-tert-butylbenzaldehyde, was refluxed with 1.25 equivalents of aminoacetaldehyde diethyl acetal in toluene in the presence of p-toluenesulfonic acid at a bath temperature of 140° C. for 1 to 3 hours with removal of water. The solvent was distilled off in vacuo, and the obtained imine was taken up in methanol and reduced with 3 equivalents of sodium borohydride for 3 hours to give the amine. After aqueous work-up the crude product was added at room temperature to a solution of an Fmoc-protected amino acid, for example Fmoc-valine, and an equimolar amount of dicyclohexylcarbodiimide (DCC) in tetrahydrofuran. After 3 hours the mixture was filtered and washed with sodium bicarbonate solution. The organic phase was separated, dried, and the solvent removed in vacuo. The residue was taken up in ethyl acetate and hydrogenated at room temperature in the presence of palladium on charcoal. Filtration and removal of the solvent in vacuo yielded the crude substituted amino acid amide, for example 2-amino-N-(4-tert-butylbenzyl)-N-(2,2-diethoxyethyl)-3-methylbutyramide, as a colorless wax which was used in the subsequent step without further purification.

b) 1 equivalent of the respective halobenzoic acid or halopyridinecarboxylic acid was reacted with 1.5 equivalents of thionyl chloride in toluene under reflux for 2 to 5 hours. After removal of the volatiles in vacuo the residue was taken up in sulfolane and reacted with 1.5 equivalents of sulfamide at 100° C. to 160° C. for 2 to 10 hours to give the nitrile which was cross-coupled with 1.25 equivalents of the primary amine, for example 3-(imidazol-1-yl)propylamine, in tetrahydrofuran in the presence of 5 mol-% of 1,1'-bis(diphenylphosphino)ferrocene palladium dichloride (Pd(dppf)Cl$_2$), 15 mol-% of 1,1'-bis(diphenylphosphino)ferrocene and 1.25 equivalents of sodium tert-butylate at reflux temperature for 1 to 5 hours. Aqueous work-up yielded the amino-substituted nitrile that was hydrolyzed with aqueous alkali in alcohol under reflux to give the amino-substituted benzoic acid or amino-substituted pyridinecarboxylic acid, respectively, which was purified by preparative HPLC on RP silica gel. The acid was then coupled for 1 hour with 1 equivalent of the substituted amino acid amide obtained in step a) by means of 1 equivalent of O-((cyano(ethoxycarbonyl)methylene)amino)-1,1,3,3-tetramethyluronium tetrafluoroborate (TOTU) in the presence of 1 to 2 equivalents of ethyldiisopropylamine in dimethylformamide at 0° C. The reaction mixture was extracted with sodium bicarbonate solution and the solvent removed in vacuo. The crude product was treated with formic acid at room temperature for 1 to 6 hours. After removal of the volatiles the compound of the formula I was purified by preparative HPLC (acetonitrile/water/trifluoroacetic acid).

Examples 17 to 35

The 2-(4-tert-butylbenzyl)-9-(3-(imidazol-1-yl)propyl)-4-isopropyl-1,2,9,9a-tetrahydro-2,4a,9-triaza-anthracene-3,10(4H)-diones of formula Ia, in which $R^4$, $R^5$, $R^6$ and $R^7$ and the stereochemical configuration at C-4 have the meanings given in Table 1, were prepared according to general procedure A, using 3-(imidazol-1-yl)propylamine, the respective 2-amino-N-(4-tert-butylbenzyl)—N-(2,2-diethoxyethyl)-3-methylbutyramide and the respective substituted 2-bromobenzoic acid. After purification by HPLC the compounds were obtained as trifluoroacetic acid salts. The retention times given in Table 1 were determined according to method HPLC A.

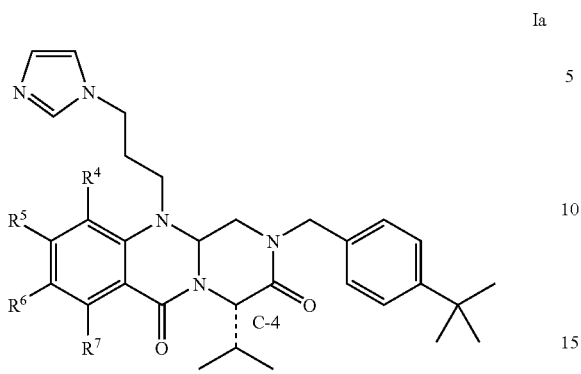

Ia

TABLE 1

Example compounds of formula Ia

| Example No. | $R^4$ | $R^5$ | $R^6$ | $R^7$ | C-4 (a) | MS (m/e) $(M + H)^+$ | Retention time (min) |
|---|---|---|---|---|---|---|---|
| 17 | H | H | H | H | RS | 514 | 4.36 |
| 18 | H | F | H | H | RS | 532 | 4.46 |
| 19 | H | H | Cl | H | R | 548 | 4.62 |
| 20 | H | $CH_3$ | H | H | R | 528 | 4.47 |
| 21 | H | H | $OCH_3$ | H | R | 544 | 4.41 |
| 22 | H | H | Cl | H | RS | 548 | 4.59 |
| 23 | H | H | F | H | RS | 532 | 4.47 |
| 24 | H | $CH_3$ | H | H | RS | 528 | 4.45 |
| 25 | H | H | $OCH_3$ | H | RS | 544 | 4.41 |
| 26 | H | —$CH(CH_3)_2$ | H | H | RS | 556 | 4.66 |
| 27 | $CH_3$ | H | H | H | S | 528 | 4.45 |
| 28 | H | H | $CH_3$ | H | RS | 528 | 4.45 |
| 29 | H | —$CO_2H$ | H | H | RS | 558 | 4.51 |
| 30 | H | H | —$CO_2H$ | H | RS | 558 | 4.47 |
| 31 | H | Cl | —$SO_2NH_2$ | H | S | 627 | 4.21 |
| 32 | H | H | —$SO_2NHCH_3$ | H | S | 607 | 4.11 |
| 33 | H | $CH_3$ | —$SO_2NH_2$ | H | S | 607 | 4.05 |
| 34 | H | Cl | —$SO_2CH_2C_6H_5$ | H | 5 | 703 | 4.54 |
| 35 | H | Cl | —$SO_2CH_3$ | H | S | 626 | 4.24 |

(a) Configuration at C-4: RS = racemic mixture, R = R configuration, S = S configuration Example 36

6-(4-tert-Butylbenzyl)-10-(3-(imidazol-1-yl)propyl)-8-isopropyl-5,6,10,10a-tetrahydro-1,6,8a,10-tetraaza-anthracene-7,9(8H)-dione trifluoroacetic acid salt

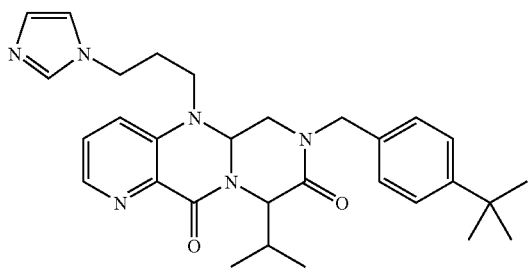

The title compound was prepared according to general procedure A, using 3-(imidazol-1-yl)propylamine, 2-amino-N-(4-tert-butylbenzyl)—N-(2,2-diethoxyethyl)-3-methyl-butyramide and 3-bromopyridine-2-carboxylic acid.

MS: m/e=515 (M+H)$^+$. Retention time (HPLC A): 4.03 min.

Example 37

6-(4-tert-Butylbenzyl)-10-(3-(imidazol-1-yl)propyl)-8-isopropyl-2-methyl-5,6,10,10a-tetrahydro-1,6,8a,10-tetraaza-anthracene-7,9(8H)-dione trifluoroacetic acid salt

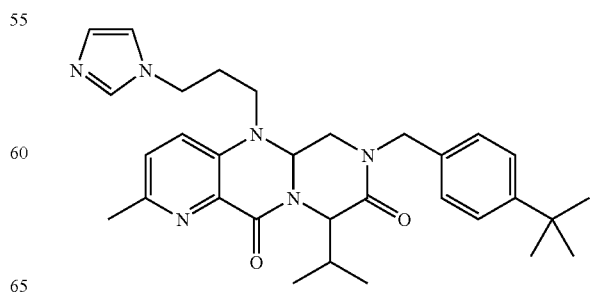

The title compound was prepared according to general procedure A, using 3-(imidazol-1-yl)propylamine, 2-amino-N-(4-tert-butylbenzyl)-N-(2,2-diethoxyethyl)-3-methylbutyramide and 3-bromo-6-methylpyridine-2-carboxylic acid.

MS: m/e=529 (M+H)$^+$. Retention time (HPLC A): 4.23 min.

Example 38

(4S)-2-(4-tert-Butylbenzyl)-4-ethyl-9-(3-(imidazol-1-yl)propyl)-6-nitro-1,2,9,9a-tetrahydro-2,4a,9-triaza-anthracene-3,10(4H)-dione trifluoroacetic acid salt

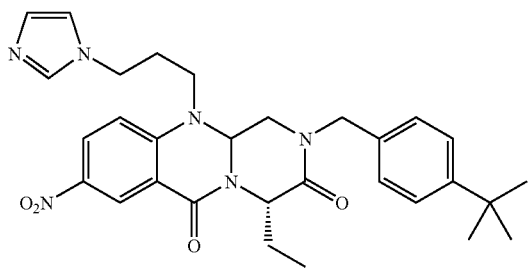

The title compound was prepared according to the procedure described in example 1, using 4-tert-butylbenzylamine instead of 4-phenylbutylamine and (S)-2-(9H-fluoren-9-ylmethoxycarbonylamino)butyric acid instead of Fmoc-L-valine.

MS: m/e=545 (M+H)$^+$.

Example 39

2-(4-tert-Butylbenzyl)-9-(3-(imidazol-1-yl)propyl)-4-isopropyl-6-nitro-1,2,9,9a-tetrahydro-2,4a,9-triaza-anthracene-3,10(4H)-dione trifluoroacetic acid salt

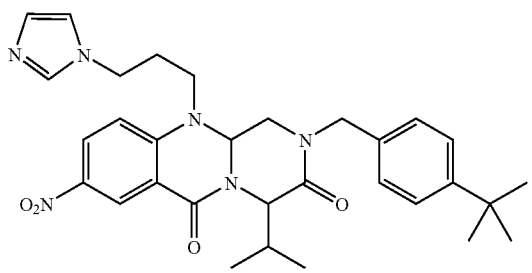

The title compound was prepared according to the procedure described in example 1, using 4-tert-butylbenzylamine instead of 4-phenylbutylamine and Fmoc-DL-valine instead of Fmoc-L-valine.

MS: m/e=559 (M+H)$^+$.

Example 40

2-(4-tert-Butylbenzyl)-4-ethyl-6-nitro-9-(2-(pyridin-4-yl)ethyl)-1,2,9,9a-tetrahydro-2,4a,9-triaza-anthracene-3,10(4H)-dione trifluoroacetic acid salt

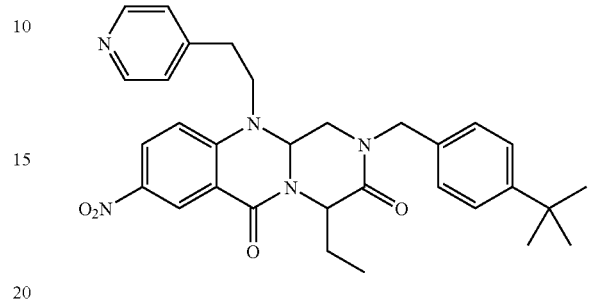

The title compound was prepared according to the procedure described in example 1, using 2-(pyridin-4-yl)ethylamine instead of 4-phenylbutylamine and 2-(9H-fluoren-9-ylmethoxycarbonylamino)butyric acid instead of Fmoc-L-valine.

MS: m/e=542 (M+H)$^+$.

Determination of the Biological Activity

Activation of eNOS Transcription

Activation of eNOS transcription was measured as described in detail by Li et al., "Activation of protein kinase C alpha and/or epsilon enhances transcription of the human endothelial nitric oxide synthase gene", Mol. Pharmacol. 53 (1998) 630. Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with the compounds.

All compounds were dissolved in sterile dimethylsulfoxide (DMSO). A final concentration of 0.5% DMSO in complete medium was allowed. Induction of reporter gene expression in these cells was measured using a standard luciferase assay system (Promega, Cat. No. E150) according to the manufacturer's instructions. Luciferase induction in cells incubated with compounds were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. EC$_{50}$ values of transcription induction ratios as a function of compound concentration were determined graphically.

The effect of compounds on eNOS-transcription was confirmed in a second assay based on eNOS protein detection. Primary human umbilical vein cord endothelial cells (HUVEC) were isolated and cultivated according to standard procedures. Confluent cells were incubated with compounds for 18 h and the effect on eNOS protein expression determined by a quantitative Western blotting procedure. After compound incubation, HUVEC were lysed in ice-cold lysis buffer containing 10 mM Tris-HCl, pH 8.0, 1% SDS and protease inhibitors. The lysate was subjected to a standard denaturating polyacrylamide gel electrophoresis and blotted to nitrocellulose membranes. Using a specific primary monoclonal antibody (Transduction Laboratories, UK) and alkaline phosphatase labelled secondary antibody (Jackson Labs), a specific eNOS protein band was visualized and quantified based on a chemofluorescence detection method.

The following results were obtained with the compounds of the formula I.

| Compound of example no. | $EC_{50}$ (µM) |
|---|---|
| 1 | 2.2 |
| 2 | 1.2 |
| 3 | 20 |
| 4 | 8 |
| 5 | 2.8 |
| 6 | 24 |
| 7 | 20 |
| 8 | 6 |
| 9 | 8.4 |
| 10 | 12 |
| 11 | 20 |
| 12 | 20 |
| 13 | 7 |
| 14 | 12 |
| 15 | 4 |
| 16 | 8 |
| 17 | 40 |
| 18 | 42 |
| 19 | 60 |
| 20 | 55 |
| 21 | 80 |
| 22 | 5 |
| 23 | 15 |
| 24 | 15 |
| 25 | 10 |
| 26 | 41 |
| 27 | 200 |
| 28 | 40 |
| 29 | 80 |
| 30 | 200 |
| 31 | 200 |
| 32 | 90 |
| 33 | 100 |
| 34 | 8 |
| 35 | 60 |
| 36 | 100 |
| 37 | 100 |
| 38 | 0.4 |
| 39 | 0.29 |
| 40 | 0.22 |

The effect of the compounds of the formula I can also be investigated in the following animal models (animal experiments are performed in accordance with the German animal protection law and the guidelines for the use of experimental animals as given by the Guide for the Care and Use of Laboratory Animals of the US National Institutes of Health).

Animals and Treatment (experiments A–C)

ApoE and eNOS deficient mice (C57BU6J background, Jackson Laboratory, Bar Harbor, Me.) are used. All animals are 10 to 12 weeks of age and weigh 22 to 28 g. Three days before surgery mice are divided into 4 groups (apoE control, n=10 to 12; apoE with test compounds, n=10 to 12; eNOS control, n=10 to 12; eNOS with test compounds, n=10 to 12) and receive either a standard rodent chow (containing 4% of fat and 0.001% of cholesterol; in the following designated as placebo group) or a standard rodent chow+test compound (10 or 30 mg/kg/day p.o.).

A) Anti-hypertensive Effect in ApoE Knockout Mice

Blood-pressure is determined in conscious mice using a computerized tail-cuff system (Visitech Systems, Apex, N.C.). After treatment of ApoE deficient mice and eNOS deficient mice with the test compounds the blood pressure is compared to the results obtained with a placebo treatment.

B) Inhibition of Neointima Formation and Atherogenesis (Femoral Artery Cuff)

After 3 day treatment of ApoE deficient mice with the respective compound (10 mg/kg/day pressed in chow), animals are anesthetized with an intraperitoneal injection of pentobarbital (60 mg/kg) followed by an intramuscular injection of xylazin (2 mg/kg) and a cuff is placed around the femoral artery as described in Moroi et al. (J Clin. Invest. 101 (1998) 1225). Briefly, the left femoral artery is dissected. A non-occlusive 2.0 mm polyethylene cuff made of PE 50 tubing (inner diameter 0.56 mm, outer diameter 0.965 mm, Becton Dickinson, Mountain View, Calif.) is placed around the artery and tied in place with two 7-0 sutures. The right femoral artery is isolated from the surrounding tissues but a cuff is not placed. Treatment with the respective compound is continued for 14 days after surgery. Then the animals are sacrificed. The aorta are taken for determination of vascular eNOS expressions by quantitative western blotting. Both femoral arteries are harvested, fixed in formalin and embedded in paraffin. 20 cross sections (10 µm) are cut from the cuffed portion of the left femoral artery and from the corresponding segment of the right artery. Sections are subjected to standard hematoxylin and eosin staining. Morphometric analyses are performed using an image analysis computer program (LeicaQWin, Leica Imaging Systems, Cambridge, GB). For each cross section the area of the lumen, the neointima and the media are determined. To this end, the neointima is defined as the area between the lumen and the internal elastic lamina and the media is defined as the area between the internal and the external elastic lamina. The ratio between the area of the neointima and the area of the media is expressed as the neointima/media ratio. The results obtained in the compound group are compared to those obtained in the placebo group.

C) Prevention of Atherosclerotic Plaque Formation in Chronic Treatment

ApoE deficient mice are treated for 16 weeks with the respective compound pressed in chow and finally sacrificed. Aortas are removed from each mouse, fixed in formalin and embedded in paraffin. Plaque formation is measured via lipid lesions formation in the aortas (from aortic arch to diaphragm) and is analyzed by oil red O staining. For quantifying the effect of the respective compound on vascular eNOS expression the femoral arteries are used in this experiment. The results obtained in the compound group are compared to those obtained in the placebo group.

D) Improvement of Coronary Function in Diseased ApoE Deficient Mice

Old Male wild-type C57BU6J mice (Charles River Wiga GmbH, Sulzfeld), and apoE deficient mice (C57BL/6J background, Jackson Laboratory, Bar Harbor, Me.) of 6 month of age and weighing 28 to 36 g are used in the experiments. Mice are divided into 3 groups (C57BL/6J, n=8; apoE control, n=8; apoE with respective compound, n=8) and receive for 8 weeks either a standard rodent chow (containing 4% of fat and 0.001% of cholesterol) or a standard rodent chow+respective compound (30 mg/kg/day p.o.). Mice are anesthetized with sodium pentobarbitone (100 mg/kg i.p.), and the hearts are rapidly excised and placed into ice-cold perfusion buffer. The aorta is cannulated and connected to a perfusion apparatus (Hugo Sachs Electronics, Freiburg, Germany) which is started immediately at a constant perfusion pressure of 60 mm Hg. Hearts are perfused in a retrograde fashion with modified Krebs bicarbonate buffer, equilibrated with 95% $O_2$ and 5% $CO_2$ and maintained at 37.5° C. A beveled small tube (PE 50) is passed through a pulmonary vein into the left ventricle and pulled through the ventricular wall, anchored in the apex by a fluted end, and connected to a tip-micromanometer (Millar 1.4 French). The left atrium is cannulated through the same pulmonary vein and the heart switched to the working mode with a constant preload pressure of 10 mm Hg and an afterload pressure of 60 mm Hg. Aortic outflow and atrial inflow are continuously measured using ultrasonic flow probes (HSE/Transonic Systems Inc.). Coronary flow is calculated as the difference between atrial flow and aortic flow. All hemodynamic data are digitized at a sampling rate of 1000 Hz and recorded with a PC using spezialized software (HEM, Notocord).

Hearts are allowed to stabilize for 30 min. All functional hemodynamic data are measured during steady state, and during volume and pressure loading. Left ventricular function curves are constructed by varying pre-load pressure. For acquisition of preload curves, afterload is set at 60 mm Hg and preload is adjusted in 5 mm Hg steps over a range of 5 to 25 mm Hg. Hearts are allowed to stabilize at baseline conditions between pressure and volume loading.

We claim:

1. A compound of formula I,

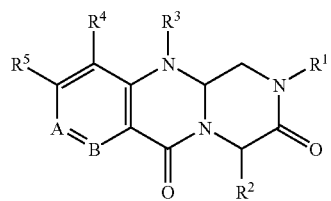

wherein:

A is $CR^6$ or N;

B is $CR^7$ or N, provided that A and B are not simultaneously N;

$R^1$ is $(C_1–C_{10})$-alkyl, $(C_3–C_8)$-cycloalkyl, $(C_2–C_{10})$-alkenyl or $(C_2–C_{10})$-alkynyl, each of which is unsubstituted or substituted by one or more identical or different substituents selected from the group consisting of halogen, cyano, $(C_3–C_8)$-cycloalkyl, phenyl, biphenylyl, naphthyl, indanyl and heteroaryl, wherein the phenyl, biphenylyl, naphthyl, indanyl and heteroaryl are each, independently, unsubstituted or substituted by one or more identical or different substituents selected from the group consisting of halogen, cyano, $(C_1–C_6)$-alkyl, trifluoromethyl, $(C_1–C_6)$-alkoxy and trifluoromethoxy;

$R^2$ is hydrogen, $(C_1–C_4)$-alkyl, trifluoromethyl, $—(CH_2)_a—(C_3–C_8)$-cycloalkyl, $—(CH_2)_a$-phenyl, $—(CH_2)_a$-imidazolyl or $—(CH_2)_a$-pyridinyl, wherein the phenyl, imidazolyl and pyridinyl are each, independently, unsubstituted or substituted by one or more identical or different substituents selected from the group consisting of halogen, cyano, $(C_1–C_6)$-alkyl, trifluoromethyl, $(C_1–C_6)$-alkoxy and trifluoromethoxy;

a is 0, 1 or 2;

$R^1$ is $—(CH_2)_b$-phenyl, $—(CH_2)_b$-imidazolyl, $—(CH_2)_b$-triazolyl, $—(CH_2)_b$-Het or $—(CH_2)_b$-pyridinyl, wherein the phenyl imidazolyl, triazolyl and pyridinyl are each, independently, unsubstituted or substituted by one or more identical or different substituents selected from the group consisting of halogen, cyano, $(C_1–C_6)$-alkyl, trifluoromethyl, $(C_1–C_6)$-alkoxy and trifluoromethoxy;

b is 1,2, 3 or 4;

$R^4$, $R^5$, $R^6$ and $R^7$ are each, independently, hydrogen, $(C_1–C_6)$-alkyl, trifluoromethyl, $(C_1–C_4)$-alkoxy, trifluoromethoxy, halogen, nitro, cyano, $—CO—R^{10}$, $—NR^8R^9$, $—NH—CO—(C_1–C_4)$-alkyl, $—SO_2—NR^8R^9$, $—SO_2—(C_1–C_4)$-alkyl or $—SO_2-(CH_2)_c$-phenyl, wherein the phenyl is unsubstituted or substituted by one or more identical or different substituents selected from the group consisting of halogen, cyano, $(C_1–C_6)$-alkyl, trifluoromethyl, $(C_1–C_6)$-alkoxy and trifluoromethoxy;

c is 0, 1 or 2;

$R^8$ and $R^9$ are each, independently, hydrogen or $(C_1–C_4)$-alkyl, $R^{10}$ is hydroxy, $(C_1–C_4)$-alkoxy or $—NR^8R^9$;

Het is a saturated 5-membered or 6-membered monocyclic heterocycle containing a ring nitrogen atom via which it is bonded, wherein the monocyclic heterocycle optionally contains a further ring heteroatom selected from the group consisting of N, O and S, and is unsubstituted or substituted by one or more identical or different substituents selected from the group consisting of $(C_1–C_4)$-alkyl and $—(CH_2)_d$-phenyl, wherein the phenyl is unsubstituted or substituted by one or more identical or different substituents selected from the group consisting of halogen, cyano, $(C_1–C_6)$-alkyl, trifluoromethyl, $(C_1–C_6)$-alkoxy and trifluoromethoxy;

d is 0, 1 or 2; and heteroaryl is an aromatic 5-membered to 10-membered, monocyclic or bicyclic heterocycle containing 1, 2, 3 or 4 identical or different ring heteroatoms selected from the group consisting of N, O and S;

or a stereoisomer or a mixture of stereoisomers thereof in any ratio, or a physiologically acceptable salt thereof;

provided that the compound of formula I is not the compound wherein

A is CH,

B is CH, $R^1$ is methyl, $R^2$ is methyl, $R^3$ is unsubstituted benzyl, $R^4$ is hydrogen, and $R^5$ is hydrogen.

2. The compound according to claim 1; wherein:

A is $CR^6$ or N;

B is $CR^7$ or N, provided that A and B are not simultaneously N;

$R^1$ is $(C_1–C_6)$-alkyl, unsubstituted or substituted by one or more identical or different substituents selected from the group consisting of $(C_3–C_6)$-cycloalkyl, phenyl, biphenylyl, naphthyl, indanyl, thienyl and pyridinyl, wherein the phenyl, biphenylyl naphthyl, indanyl, thienyl and pyridinyl are each, independently, unsubstituted or substituted by one or more identical or different substituents selected from the group consisting of fluorine, chlorine, bromine, cyano, $(C_1–C_6)$-alkyl, trifluoromethyl, $(C_1–C_4)$-alkoxy and trifluoromethoxy;

$R^2$ is hydrogen, $(C_1–C_4)$-alkyl, trifluoromethyl, $—(CH_2)_a-(C_3–C_8)$-cycloalkyl, $—(CH_2)_p$-phenyl, $—(CH_2)_a$-imidazolyl or $—(CH_2)_a$-pyridinyl, wherein the phenyl, imidazoyl and pyridinyl are each, independently, unsubstituted or substituted by one or more identical or different substituents selected from the group consisting of fluorine, chlorine, bromine, cyano, $(C_1-C_4)$-alkyl, trifluoromethyl, $(C_1-C_4)$-alkoxy and trifluoromethoxy;

a is 0 or 1;

$R^3$ is $-(CH_2)_b$-phenyl, $-(CH_2)_b$-imidazolyl, $-(CH_2)_b$-triazolyl, $-(CH_2)_b$-Het or $-(CH_2)_b$-pyridinyl wherein the phenyl, imidazoyl, triazolyl and pyridinyl are each, independently, unsubstituted or substituted by one or more identical or different substituents selected from the group consisting of fluorine, chlorine, bromine, cyano, $(C_1-C_4)$-alkyl, trifluoromethyl, $(C_1-C_4)$-alkoxy and trifluoromethoxy;

b is 1, 2, 3 or 4;

$R^4$, $R^5$, $R^6$ and $R^7$ are each, independently, hydrogen, $(C_1-C_4)$-alkyl, trifluoromethyl, methoxy, fluorine, chlorine, nitro, $-CO-R^{10}$, $-NR^8R^9$, $-NH-CO$-methyl, $-SO_2NR^8R^9$, $-SO_2$-methyl or $-SO_2-CH_2$-phenyl, wherein the phenyl is unsubstituted or substituted by one or more identical or different substituents selected from the group consisting of fluorine, chlorine, bromine, cyano, $(C_1-C_4)$-alkyl, trifluoromethyl, $(C_1-C_4)$-alkoxy and trifluoromethoxy;

$R^8$ and $R^9$ are each, independently, hydrogen or methyl;

$R^{10}$ is hydroxy, $(C_1-C_4)$-alkoxy or $-NR^8R^9$,

Het is a saturated 5-membered or 6-membered monocyclic heterocycle containing a ring nitrogen atom via which it is bonded, wherein the monocyclic heterocycle optionally contains a further ring heteroatom selected from the group consisting of N, O and S, and is unsubstituted or substituted by one or more identical or different substituents selected from the group consisting of $(C_1-C_4)$-alkyl and $-(CH_2)_d$-phenyl, wherein the phenyl is unsubstituted or substituted by one or more identical or different substituents selected from the group consisting of fluorine, chlorine, bromine, cyano, $(C_1-C_4)$-alkyl, trifluoromethyl, $(C_1-C_4)$-alkoxy and trifluoromethoxy; and d is 0, 1 or 2, or a stereoisomer or a mixture of stereoisomers thereof in any ratio, or a physiologically acceptable salt thereof.

3. The compound according to claim 1, wherein:

A is $CR^6$ or N;

B is $CR^7$ or N, provided that A and B are not simultaneously N;

$R^1$ is $(C_1-C_4)$-alkyl substituted by phenyl, wherein the phenyl is unsubstituted or substituted by one or more identical or different substituents selected from the group consisting of fluorine, chlorine, bromine, cyano, $(C_1-C_4)$-alkyl, trifluoromethyl, $(C_1-C_4)$-alkoxy and trifluoromethoxy;

$R^2$ is hydrogen, $(C_1-C_4)$-alkyl, trifluoromethyl or $(C_3-C_6)$-cycloalkyl;

$R^3$ is $-(CH_2)_b$-imidazolyl, $-(CH_2)_b$-triazolyl or $-(CH_2)_b$-pyrimidyl, wherein imidazolyl, triazolyl and pyridinyl are all unsubstituted or substituted by one or more identical or different $(C_1-C_4)$-alkyl substituents;

b is 1, 2, 3 or 4;

$R^4$ and $R^7$ are each, independently, hydrogen, $(C_1-C_4)$-alkyl, trifluoromethyl, methoxy, fluorine or chlorine;

$R^5$ and $R^6$ are each, independently, hydrogen, $(C_1-C_4)$-alkyl, trifluoromethyl, methoxy, fluorine, chlorine, nitro, $-CO-R^{10}$, $-NR^8R^9$, $-NH-CO$-methyl, $-SO_2-NR^8R^9$, $-SO_2$-methyl or $-SO_2$-phenyl;

$R^8$ and $R^9$ are each, independently, hydrogen or methyl; and $R^{10}$ is hydroxy, $(C_1-C_2)$-alkoxy or $-NR^8R^9$, or a stereoisomer or a mixture of stereoisomers thereof in any ratio, or a physiologically acceptable salt thereof.

4. The compound according to claim 1, wherein:

A is $CR^6$; and

B is $CR^7$, or a stereoisomer or a mixture of stereoisomer is thereof in any ratio, or a physiologically acceptable salt thereof.

5. The compound according to claim 1, wherein one of A and B is nitrogen and the other is $CR^6$ or $CR^7$, or a stereoisomer or a mixture of stereoisomers thereof in any ratio, or a physiologically acceptable salt thereof.

6. A pharmaceutical composition comprising a pharmaceutically effective amount of the compound according to claim 1 or a stereoisomer or a mixture of stereoisomers thereof in any ratio, or a physiologically acceptable salt thereof, and a pharmaceutically acceptable carrier.

7. A method for treating a cardiovascular disease, stable or unstable angina pectoris, coronary heart disease, Prinzmetal angina, acute coronary syndrome, heart failure, myocardial infarction, stroke, endothelial dysfunction, atherosclerosis, endothel damage after PTCA, hypertension, essential hypertension, pulmonary hypertension, secondary hypertension, or renovascular hypertension, in a patient in need thereof, comprising administering to the patient a pharmaceutically effective amount of the compound according to claim 1, or a stereoisomer or a mixture of stereoisomers thereof in any ratio, or a physiologically acceptable salt thereof.

8. A process for the preparation of the compound of the formula I as defined in claim 1 or wherein one or more functional groups present therein can be in protected form or in the form of a precursor group, comprising treating a compound of the formula VI,

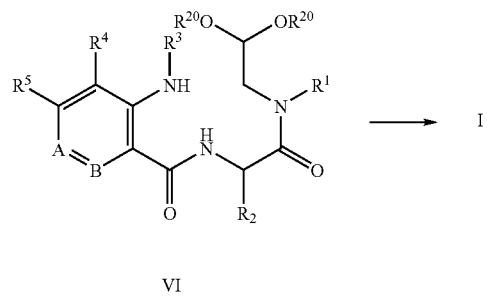

wherein A, B, $R^1$, $R^2$, $R^3$, $R^4$ and $R^5$ are as defined in claim 1 or one or more functional groups present therein can be in protected form or in the form of a precursor group and $R^{20}$ is $(C_1-C_4)$-alkyl, with an acid.

* * * * *